(12) United States Patent
Cowe

(10) Patent No.: US 10,232,124 B2
(45) Date of Patent: Mar. 19, 2019

(54) RE-USEABLE INJECTOR DEVICE FOR SYRINGE

(71) Applicant: Teva Pharmaceutical Industries, Ltd., Petach Tikva (IL)

(72) Inventor: Toby Cowe, Cheltenham (GB)

(73) Assignee: Teva Pharmaceutical Industries, Ltd., Petach Tikva (IL)

( * ) Notice: Subject to any disclaimer, the term of this patent is extended or adjusted under 35 U.S.C. 154(b) by 0 days.

(21) Appl. No.: 16/059,860

(22) Filed: Aug. 9, 2018

(65) Prior Publication Data

US 2018/0344941 A1 Dec. 6, 2018

Related U.S. Application Data

(60) Division of application No. 15/691,380, filed on Aug. 30, 2017, now Pat. No. 10,071,206, which is a continuation of application No. 14/048,601, filed on Oct. 8, 2013, now Pat. No. 9,827,374, which is a
(Continued)

(51) Int. Cl.

| | |
|---|---|
| *A61M 5/315* | (2006.01) |
| *A61M 5/46* | (2006.01) |
| *A61M 5/20* | (2006.01) |
| *A61M 5/31* | (2006.01) |
| *A61M 5/32* | (2006.01) |

(52) U.S. Cl.
CPC .......... *A61M 5/31595* (2013.01); *A61M 5/20* (2013.01); *A61M 5/2033* (2013.01); *A61M 5/46* (2013.01); *A61M 5/3157* (2013.01); *A61M 5/3204* (2013.01); *A61M 2005/202* (2013.01); *A61M 2005/206* (2013.01); *A61M 2005/208* (2013.01); *A61M 2005/2073* (2013.01); *A61M 2005/2086* (2013.01); *A61M 2005/3125* (2013.01); *A61M 2005/3126* (2013.01); *A61M 2205/581* (2013.01); *A61M 2205/583* (2013.01); *A61M 2205/586* (2013.01)

(58) Field of Classification Search
CPC .. A61M 5/31595; A61M 5/2033; A61M 5/28; A61M 5/281; A61M 2005/2418; A61M 2005/208
See application file for complete search history.

(56) References Cited

U.S. PATENT DOCUMENTS

2006/0270986 A1* 11/2006 Hommann .......... A61M 5/2033
604/136
2010/0160894 A1* 6/2010 Julian ................. A61M 5/2033
604/506
(Continued)

*Primary Examiner* — Laura A Bouchelle
(74) *Attorney, Agent, or Firm* — Merchant & Gould P.C.

(57) ABSTRACT

An injector device includes an injector body that receives a syringe; and an injection assembly being configured to dispense medicament from the syringe in a dispensation step. Certain types of injector devices include a sudden completion indicator that indicates when the injection is completed. Certain types of injector devices are configured to dispense two different medicament formulations having different viscosities from syringes without making any changes to the injector devices other than to switch out the syringes. Certain types of injector devices include safety arrangements that inhibit firing of the injector device until front and rear housing assemblies are disposed in predetermined rotational and axial positions relative to each other.

27 Claims, 19 Drawing Sheets

Related U.S. Application Data continuation of application No. 13/790,531, filed on Mar. 8, 2013, now Pat. No. 8,591,463.

(56) References Cited

U.S. PATENT DOCUMENTS

2011/0178500 A1\* 7/2011 Shang .............. A61M 5/2033
                                                                604/506
2011/0202011 A1\* 8/2011 Wozencroft ........ A61M 5/2033
                                                                604/192

\* cited by examiner

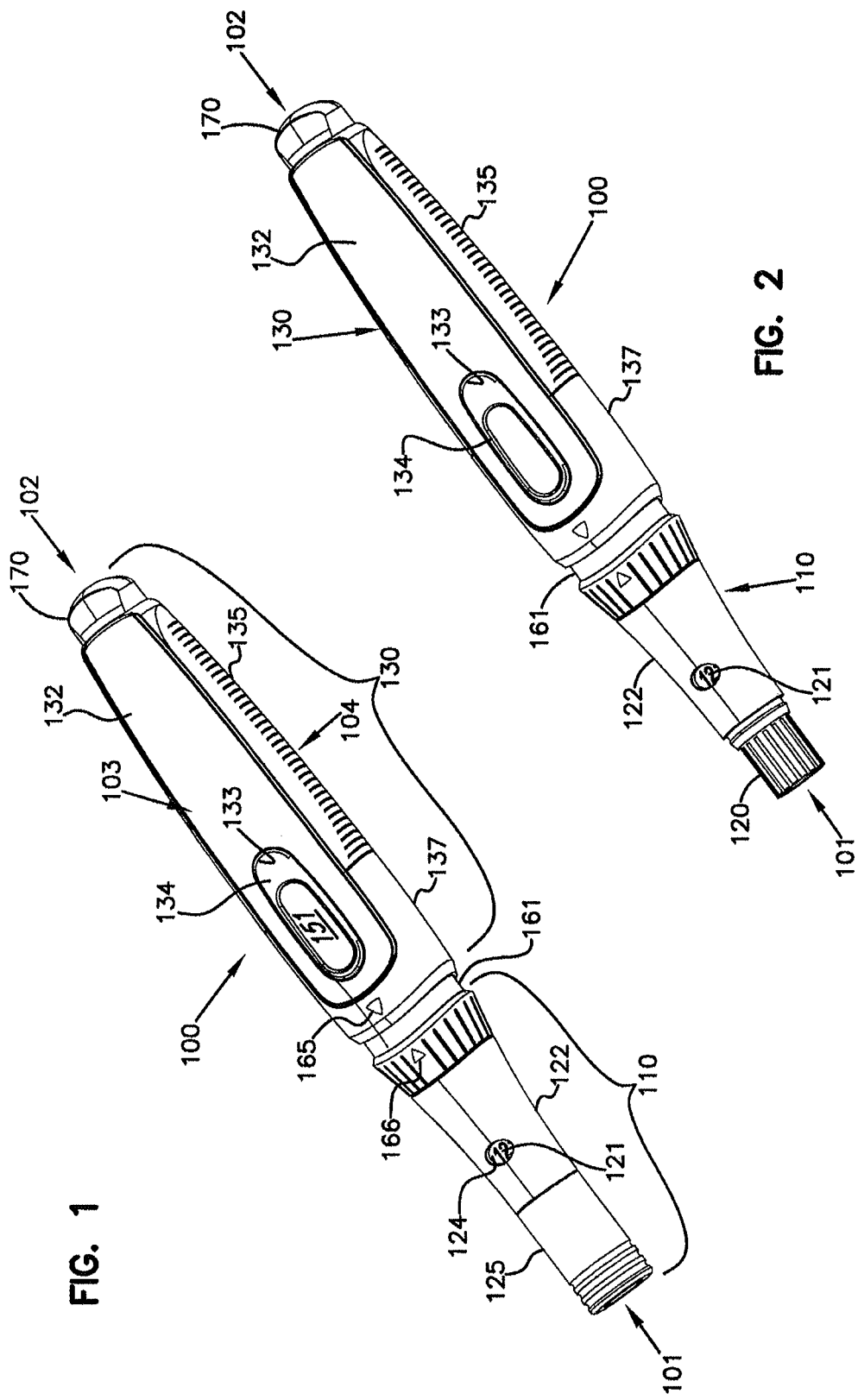

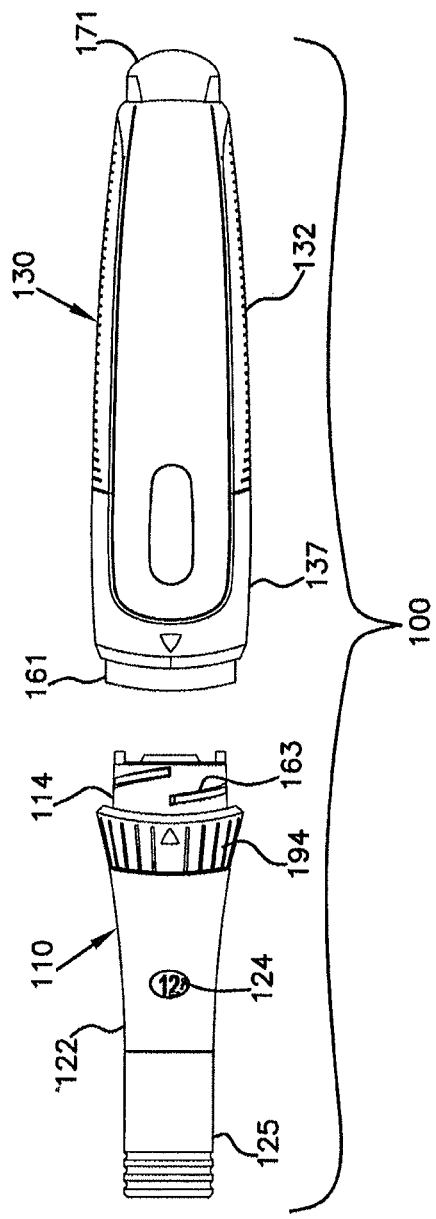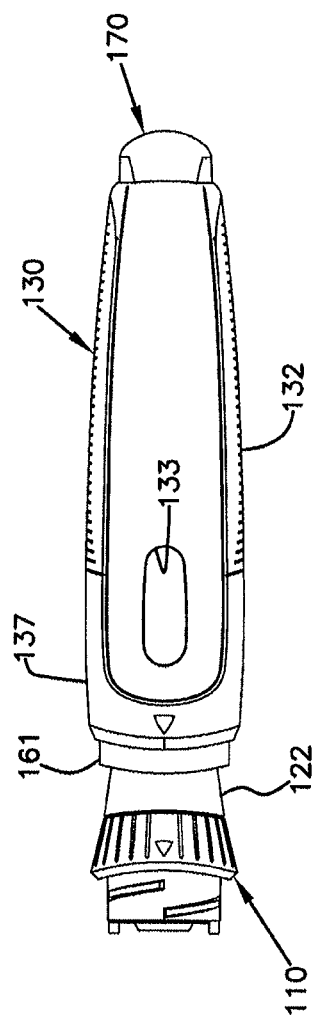
FIG. 4
FIG. 6

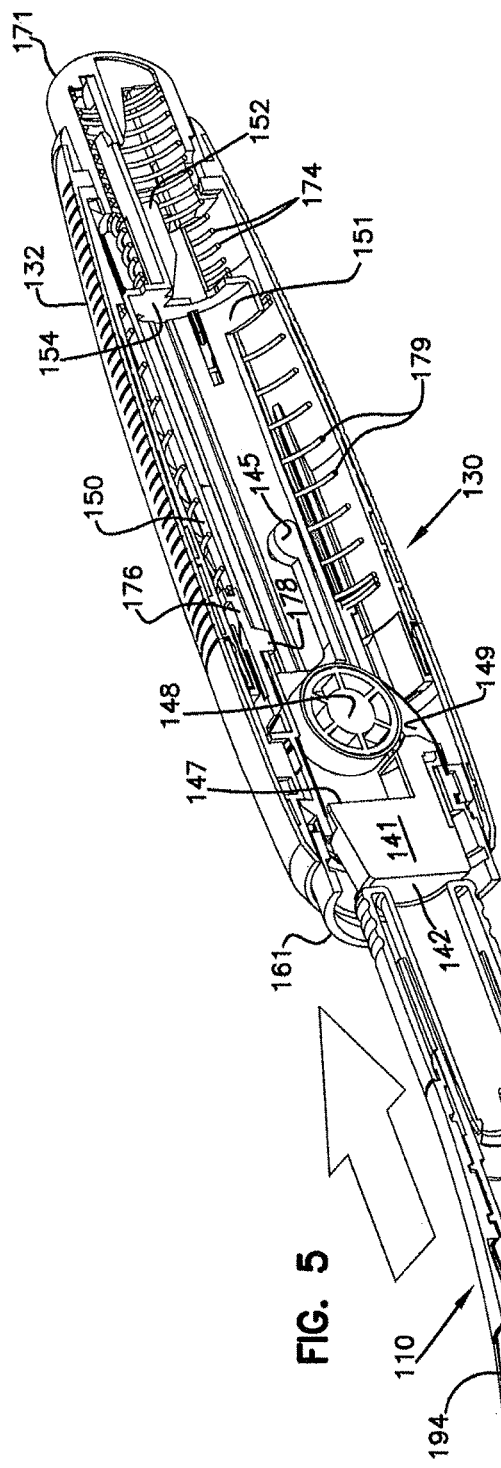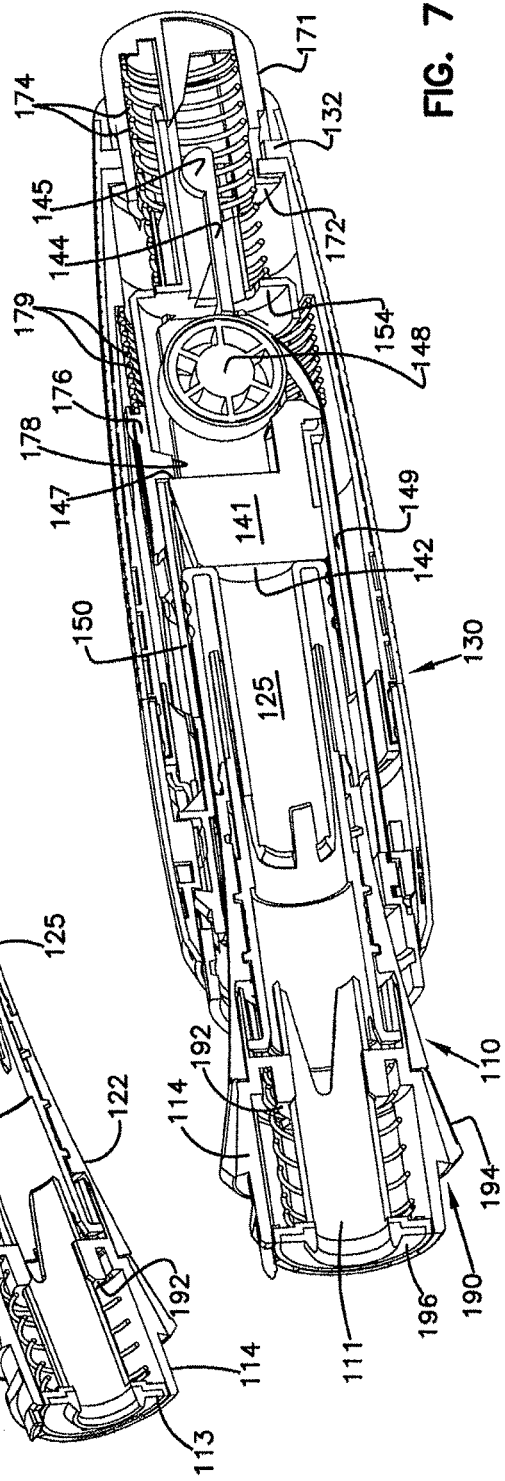

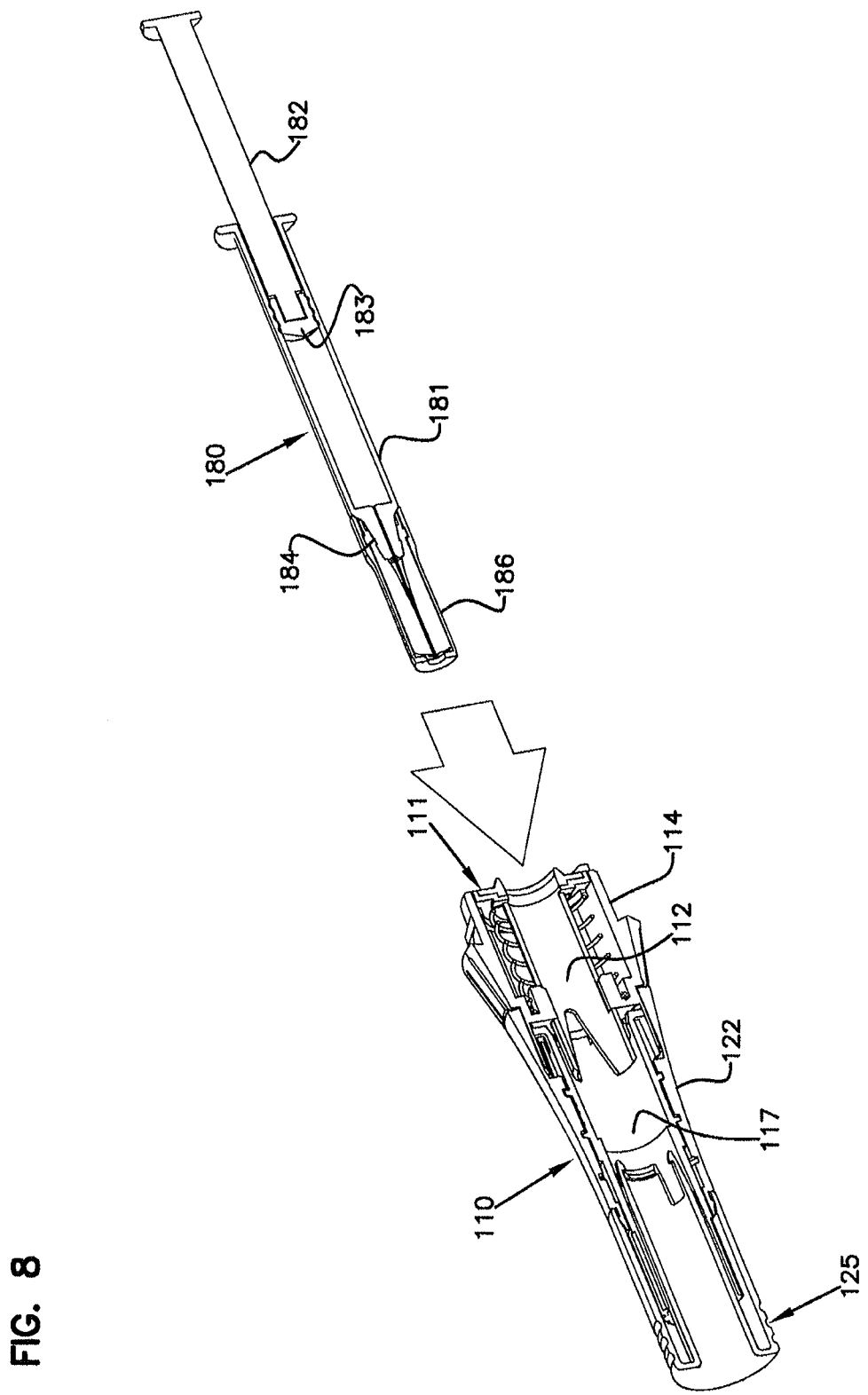

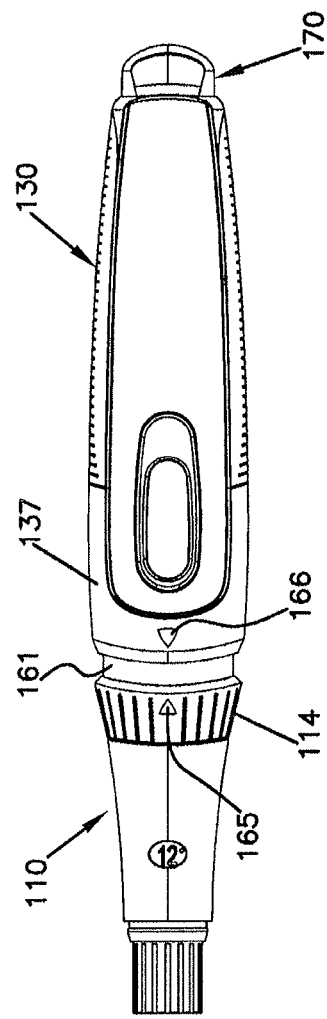
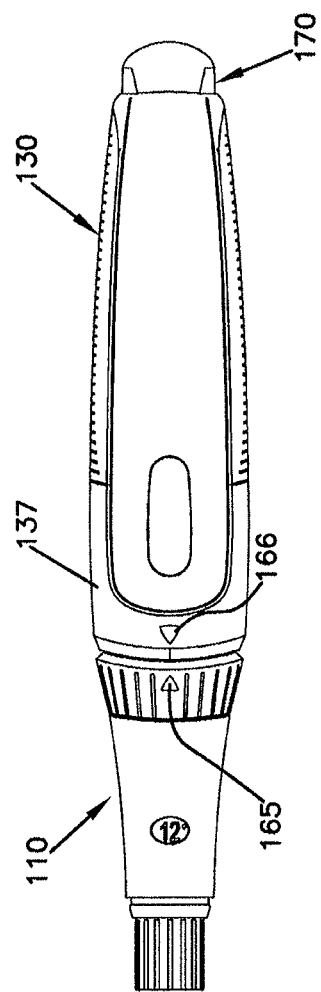
FIG. 13
FIG. 14

RE-USEABLE INJECTOR DEVICE FOR SYRINGE

CROSS REFERENCE TO RELATED APPLICATIONS

This application is a divisional of application Ser. No. 15/691,380, filed Aug. 30, 2017, which is a continuation of application Ser. No. 14/048,601, filed Oct. 8, 2013, now U.S. Pat. No. 9,827,374, which is a continuation of application Ser. No. 13/790,531, filed Mar. 8, 2013, now U.S. Pat. No. 8,591,463, which applications are incorporated herein by reference in their entirety.

BACKGROUND

Medicament can be dispensed from a syringe using an injector device. Some injector devices are spring-loaded so that a user need only actuate a trigger to cause dispensation of the medicament. Certain types of injector devices also automatically inject a needle into an injection site prior to dispensing of the medicament. For example, certain types of injector devices trigger actuation when a front of the injector device is pushed against the injection site. Certain types of injector devices are "one-shot" devices. Other types of injector devices are configured to be reused by enabling a spent syringe to be switched out for a replacement syringe. Certain types of injector devices include indicators that provide an indication of how many times the injector device has injected medicament or how much medicament has been dispensed.

SUMMARY

In accordance with some aspects of the disclosure, an injector device includes a first housing assembly configured to hold a syringe; a second housing assembly; a locking member; and an interlock assembly configured to rotatably attach the first housing assembly to the second housing assembly in a particular rotational position. The second housing assembly includes an outer housing and an inner housing. The inner housing is configured to be axially fixed relative to the first housing assembly. The outer housing is configured to move axially relative to the first housing assembly between an extended position and a retracted position. The second housing assembly includes an injection assembly configured to operate the syringe to inject medicament from the syringe. The second housing assembly includes a trigger member configured to fire the injection assembly only when the outer housing is in the retracted position. The second housing assembly includes a biasing member that biases the outer housing into the extended position. The locking member fixedly holds the outer housing in the extended position. The interlock assembly is configured to release the locking member so that the outer housing is movable relative to the first housing assembly to the retracted position against the bias of the biasing member.

In accordance with other aspects of the disclosure, an injector device includes an injector body including a front assembly and a rear assembly that cooperate to define an interior; a syringe; and an injection assembly disposed within the interior of the injector body. The front assembly includes a forward housing, a syringe carrier that is movable relative to the forward housing between a rearward position and a forward position, a first damper disposed at a rear of the forward housing, and a second damper disposed at a rear of the syringe carrier. The syringe carrier engages the first damper when in the forward position and the syringe carrier is spaced from the first damper when in the rearward position. The syringe is configured to be coupled to the syringe carrier for movement therewith. The syringe includes an ampoule, a needle, and a plunger. The needle extends from a first end of the ampoule and the plunger extends from a second end of the ampoule. At least a portion of the ampoule engages the second damper. The ampoule is configured to hold a common volume of either one of at least two different medicament formulations without modification to the injector device. A first of the two different medicament formulations has a first viscosity and a second of the two different medicament formulations has a second viscosity that is different from the first viscosity. The injection assembly is configured to dispense the medicament formulation held by the syringe. The injection assembly includes a ram driven by a constant force spring. Releasing the constant force spring drives the syringe carrier from the rearward position to the forward position until the syringe carrier engages the first damper. The constant force spring drives the plunger within the ampoule of the syringe after the syringe carrier is in the forward position. The first and second dampers cooperate to inhibit breaking of the ampoule during movement of the syringe carrier and movement of the plunger.

In accordance with certain aspects of the disclosure, an injector device includes a sudden completion indicator member disposed within the interior of an injector body. The sudden completion indicator member is configured to move relative to the injector body between a first position and a second position. The sudden completion indicator member is not visible through a window in the injector body when in the first position and is visible through the window when in the second position. Movement of the sudden completion indicator member from the first position to the second position is actuated at completion of the dispensation step.

A variety of additional inventive aspects will be set forth in the description that follows. The inventive aspects can relate to individual features and to combinations of features. It is to be understood that both the forgoing general description and the following detailed description are exemplary and explanatory only and are not restrictive of the broad inventive concepts upon which the embodiments disclosed herein are based.

BRIEF DESCRIPTION OF THE DRAWINGS

The accompanying drawings, which are incorporated in and constitute a part of the description, illustrate several aspects of the present disclosure. A brief description of the drawings is as follows:

FIG. 1 is a front perspective view of an example injector device being configured in accordance with the principles of the present disclosure;

FIG. 2 is a front perspective view of the injector device of FIG. 1 with a sheath remover removed from the injector device;

FIG. 4 is a side elevational view of the injector device of FIG. 1 with a front assembly axially separated from a rear assembly;

FIG. 5 is an axial cross-sectional view of the injector device of FIG. 4 with the front assembly flipped to face the rear assembly;

FIG. 6 is a side elevational view of the injector device of FIG. 4 with a front end of the front assembly inserted into a front end of the rear assembly to arm an injection system of the injector device;

FIG. 7 is an axial cross-sectional view of the injector device of FIG. 6;

FIG. 8 is an axial cross-section of the front assembly of the injector device of FIG. 1 with a syringe shown being loaded into the front assembly;

FIG. 13 is a side elevational view of the injector device of FIG. 1 with a rear housing disposed in an extended position;

FIG. 14 is a side elevational view of the injector device of FIG. 13 with the rear housing disposed in a retracted position;

DETAILED DESCRIPTION

Figure 3:
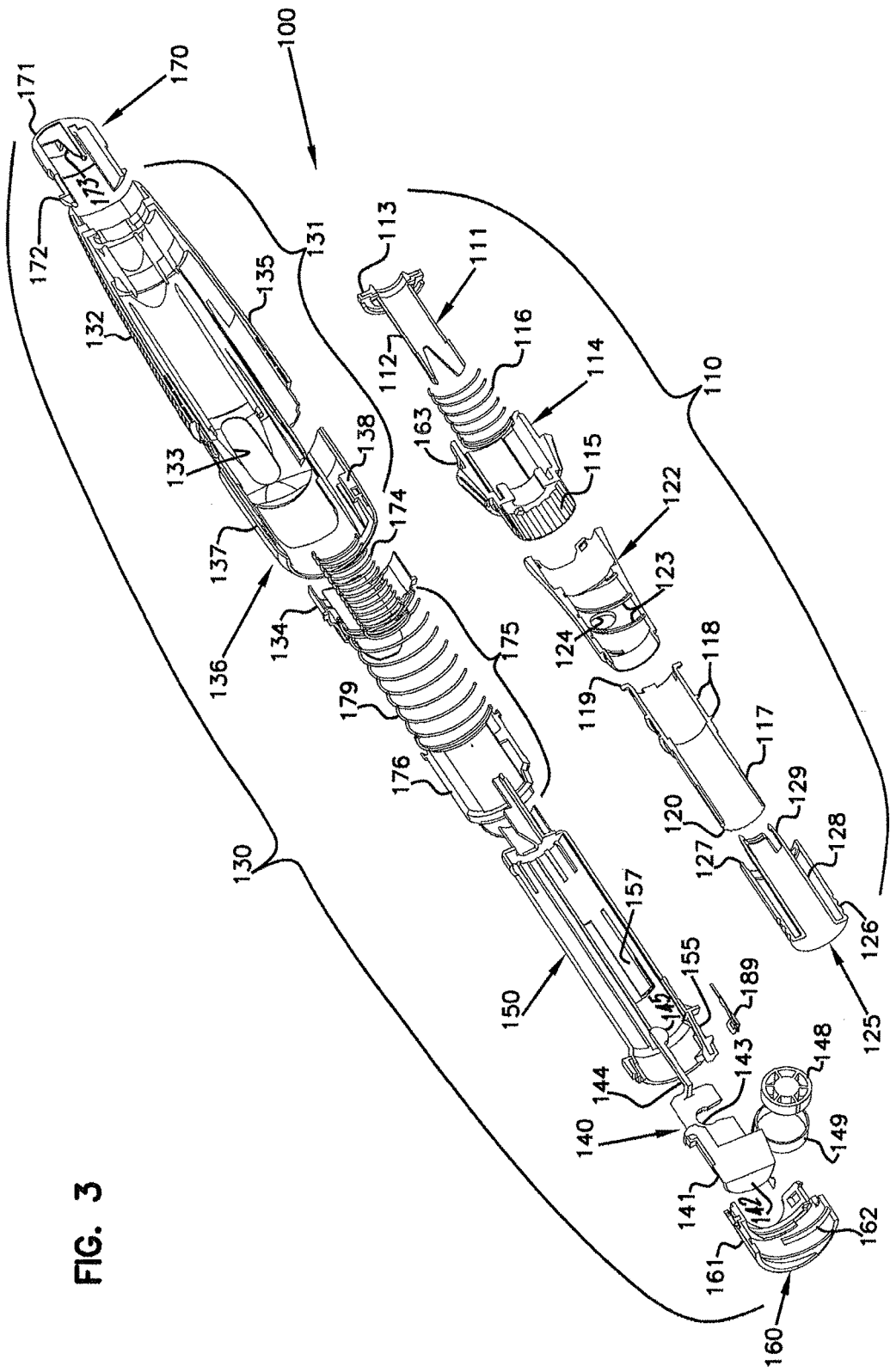
FIG. 3 is an exploded view of the injector device of FIG. 1.

Reference will now be made in detail to exemplary aspects of the present disclosure that are illustrated in the accompanying drawings. Wherever possible, the same reference numbers will be used throughout the drawings to refer to the same or like parts.

In general, the disclosure is directed to an injector device configured to hold a syringe and an injection assembly. The injection assembly is configured to dispense medicament from the syringe (i.e., emit fluid from the syringe) in a dispensation step. In some implementations, the injection assembly also is configured to move the syringe from a retracted position to an extended position to inject the syringe (i.e., insert the needle at the injection site) in an injection step. In certain implementations, the injector device is re-useable. For example, the syringe may be removed after use and may be replaced with a new syringe.

In accordance with some implementations, the injector device has a completion indicator that indicates that the medicament has been dispensed and that the user may withdraw the needle from the injection site. In certain implementations, the completion indicator is a sudden completion indicator. For example, the completion indicator actuate only at the completion of the dispensation step. As the term is used herein, "at completion" refers to the timeframe including the moment of completion, a time immediately after the moment of completion, and times within a few milliseconds before and after completion (e.g., due to tolerance within the injector device). Until dispensation is complete, the display provided by the sudden completion indicator does not change. In some implementations, the sudden completion indicator includes a window through which a color change is visible when dispensation is complete. In certain implementations, the sudden completion indicator includes an audible sound produced when dispensation is complete. In certain implementations, the sudden completion indicator includes both a color change and an audible sound.

In accordance with some implementations, the injector device is configured to be used with syringes that may have either one of at least two different formulations. The formulation used in the syringes may be switched between the two formulations without adjustment to the injector device. For example, the injector device may be used with a first syringe having 20 milligrams of a particular medicament in a particular volume. The first syringe may be replaced after injection with a second syringe containing 40 milligrams of a medicament in the same volume. The injector device may inject and dispense the second syringe without any adjustments made to the injector device.

The same injector device can receive either the first or second syringe. For example, the dimensions of the first syringe and the second syringe may be substantially identical. No parts of the injector device need to be resized, moved, or otherwise modified to switch which formulation is being loaded. For example, the same constant force spring, the same ram placement, and the same plunger depth may be used with both syringes. Accordingly, before each injection, a user can choose whether to load the injector device with the first formulation or with the second formulation. Damping areas on a syringe carrier and carrier holder inhibit breaking of the syringe during injection and dispensation. For example, the damping areas may reduce the rate or frequency of syringe breakage (e.g., cracking, fracturing, and/or shattering of the ampoule, deformation or displacement of the needle hub relative to the ampoule, or other damage to the syringe) during injection as compared to syringes that do not include the damping areas.

In accordance with some implementations, the injector device includes safety arrangements that inhibit firing of the injector device until the injector device is correctly assembled, pressed against the injection site with a predetermined amount of force, and a trigger is actuated. For example, pressing a trigger button of the injector device when the predetermined amount of force is not being applied to the injector device would not actuate the injection assembly to inject the syringe or dispense medicament. In some implementations, the injector device includes a front assembly and a rear assembly that are rotationally aligned and axially moved towards each other before actuating the trigger will fire the injection assembly.

FIGS. 1 and 2 illustrate an example injector device 100 extending between a front 101 and a rear 102. The injector device 100 has opposite side surfaces 103 that extend between the front 101 and the rear 102. In general, the injector device 100 is configured to dispense medicament from the front 101 when triggered at the rear 102. The injector device 100 also has opposite end surfaces 104 that extend between the side surfaces 103 and between the front 101 and rear 102. In some implementations, the side surfaces 103 have a greater cross-dimension than the end surfaces 104.

Figure 12:
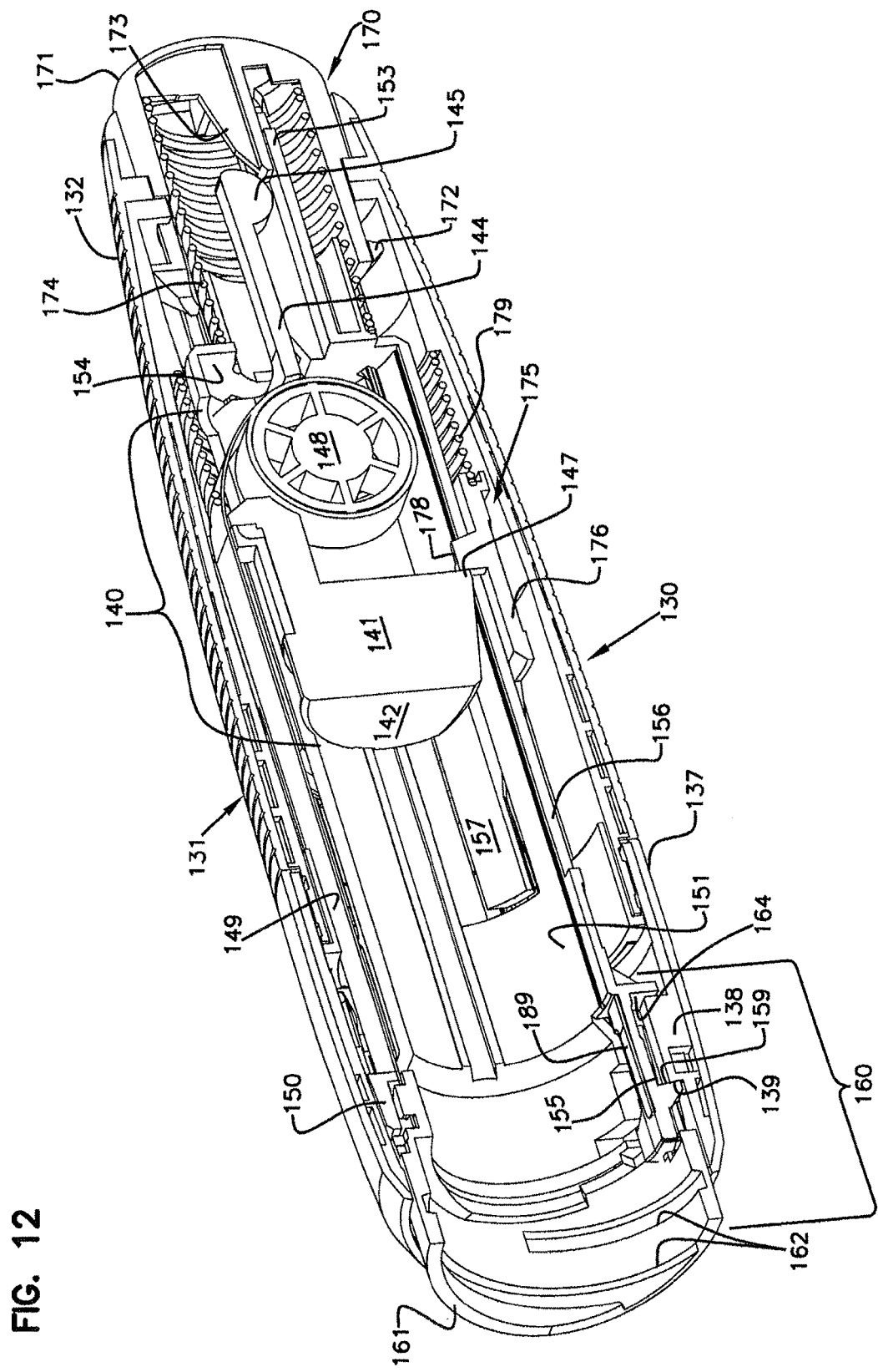
FIG. 12 is a perspective view of the rear assembly of FIG. 4 shown in axial cross-section and isolated from the front assembly.

The injector device 100 includes a front assembly 110 and a rear assembly 130 that couple together. The front assembly 110 is configured to hold the syringe 180 (FIG. 8). The rear assembly 130 is configured to hold the injection assembly 140 (FIG. 12). In some implementations, the front and rear assemblies 110, 130 can be releasably coupled together to provide access to an interior of the injector device 100. For example, the front assembly 110 may be threaded, latched, snap-fit, friction-fit, or otherwise releasably coupled onto the rear assembly 130. Releasing the front assembly 110 from the rear assembly 130 enables a user to replace the syringe within the front assembly 110.

As shown in FIG. 3, the front assembly 110 includes a syringe carrier 111 configured to be slideably mounted within a carrier support 114 between forward and rearward positions. The syringe carrier 111 is configured to hold the syringe 180 (FIG. 8) so that a front of the syringe 180 extends forwardly of the carrier 111 (e.g., see FIG. 10). When the syringe carrier 111 is in the rearward position, the syringe 180 does not protrude from the front 101 of the injector device 100 (e.g., see FIG. 15). When the syringe carrier 111 is in the forward position, the syringe (i.e., at least part of the needle 185) protrudes from the front 101 of the injector device 100 (e.g., see FIG. 21). A carrier spring 116 biases the syringe carrier 111 towards the rear position. In particular, a first end of the carrier spring 116 abuts against a hub 113 of the syringe carrier 111 and a second end of the spring 116 abuts against an interior shoulder within the carrier support 114. An intermediate part of the carrier spring 116 extends over a support section 112 of the syringe carrier 111.

In some implementations, a damper arrangement 190 is provided on the syringe carrier 111 and carrier support 114 to inhibit breaking of the syringe 180 (FIG. 8) during injection and dispensation (e.g., see FIG. 7). For example, the damper arrangement 190 may reduce a risk of the syringe 180 breaking when the syringe 180 is advanced within the front assembly 110 and/or when a plunger 182 (FIG. 8) is advanced within the syringe 180. In some implementations, the damper arrangement 190 includes one or more dampers disposed on the front housing assembly 110 and/or syringe carrier 111. In various implementations, the dampers are formed of a resilient material, such as rubber, foam, or gel.

In some implementations, a first damper 192 is positioned at least at a rear-ward facing surface of the carrier support 114 (FIG. 7). The first damper 192 is configured to engage the syringe carrier 111 when the syringe carrier 111 is in the forward position. The first damper 192 absorbs energy from the syringe carrier 111 when the syringe carrier 111 reaches the forward position. Accordingly, the first damper 192 inhibits that energy from being transferred to the syringe 180. In some implementations, second damper 196 is disposed on the syringe carrier 111 to engage the syringe 180 (FIG. 7). The second damper 196 cooperates with the first damper 192 to inhibit breaking of the syringe 180 when the syringe carrier 111 engages the carrier support in the forward position and/or when the syringe plunger is fully depressed within the syringe 180.

Figure 9:
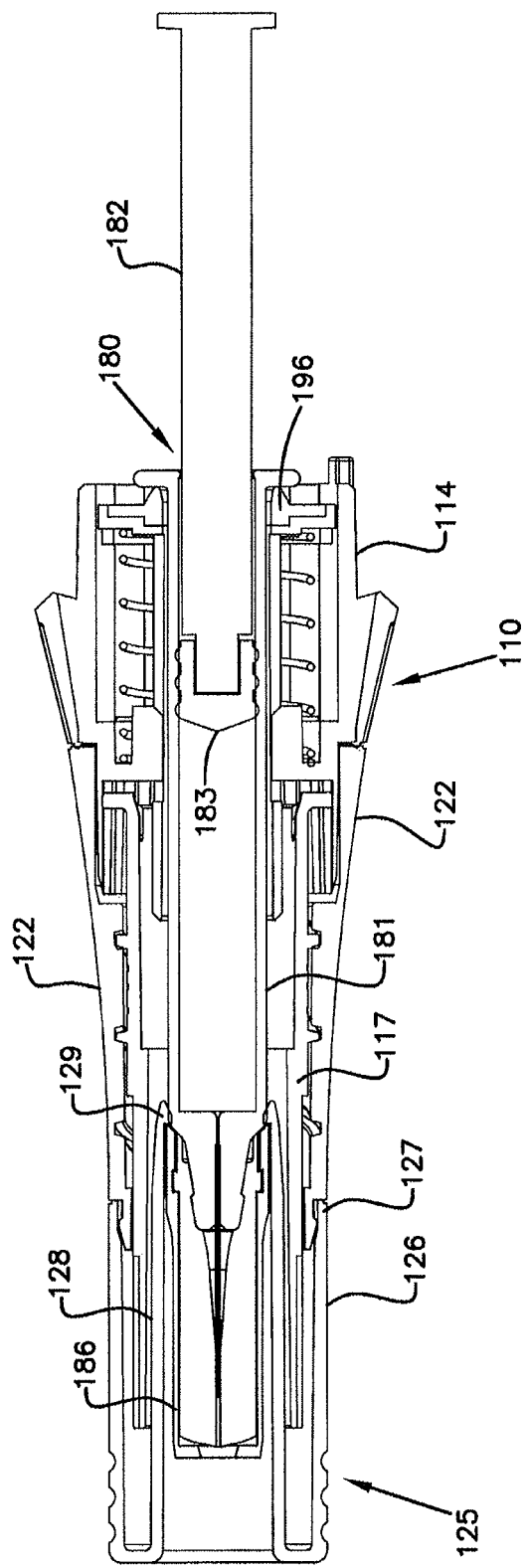
FIG. 9 is an enlarged, cross-sectional view of the front end of the injector device of FIG. 1 with the syringe loaded so that a sheath remover of the front assembly engages a needle sheath.

In some implementations, the first damper 192 includes one or more gasket sections disposed on the carrier support 114 and facing the syringe carrier 111. In other implementations, the first damper 192 is part of a grip member 194 (FIG. 5) that also extends over an exterior surface of the front assembly 110. In certain implementations, the grip member 194 is a soft/resilient/compressible material (e.g., rubber) over-molded or otherwise formed over an exterior of the carrier support 114. In some implementations, the second damper 196 includes a gasket ring disposed at a through-passage of the syringe carrier 111. In certain implementations, at least part of the second damper 196 seats on a rearward-facing surface of the syringe carrier 111. The rear end of the syringe 180 seats on the second damper 196 (FIG. 9).

The front assembly 110 also includes a depth adjustment assembly that controls a distance the needle 185 (FIG. 10) of the syringe 180 protrudes from the front 101 of the injector device 100 during injection. Referring back to FIG. 3, the depth adjustment assembly includes a depth adjuster 117 disposed within a depth adjuster housing 122 that couples to the carrier support 114. For example, the depth adjuster 117 may define outer threads 118 that engage inner threads 123 of the housing 122 (FIG. 3). In some implementations, latch arms 119 of the depth adjuster 117 may interact with notched inner surface 115 (FIG. 3) of the carrier support 114 to define discrete rotational positions of the depth adjuster 117 relative to the housing 122. Each discrete rotational position corresponds with a different needle depth. In other implementations, the notched inner surface may be provided on the adjuster housing 122.

Indicia 121 (FIGS. 1 and 2) are provided at an exterior surface of the depth adjuster 117 to indicate how far the needle is set to protrude. For example, a series of numbers indicating length or distance may be arranged in a helical pattern around the exterior of the depth adjuster 117. The adjuster housing 122 defines a window 124 through which the depth adjuster 117 is visible (FIG. 1). As the depth adjuster 117 threads along the adjuster housing 122, the indicia 121 cycle beneath the window 124. In some implementations, the indicia 121 are spaced to correspond with the discrete rotational positions defined by the notched inner surface 115 of the carrier support 114. For example, in some implementations, a new indicium 121 is visible through the window 124 at each rotational position of the depth adjuster 117. In other implementations, a new indicium 121 is visible at predetermined rotational positions. In some implementations, the indicia 121 are sufficiently large to facilitate reading of the indicium 121 by a user. For example, at least some of the indicium 121 may be 4 mm high.

The depth adjuster 117 defines a grip surface 120 (FIG. 2) towards the front 101 of the injector device 100. To adjust the depth of the syringe needle, a user grasps the grip surface 120 of the depth adjuster 117 to rotate the depth adjuster 117 clockwise or counter-clockwise. Movement in one direction increases the needle depth by moving the depth adjuster 117 rearwardly relative to the adjuster housing 122. Movement in the other direction decreases the needle depth by moving the depth adjuster 117 forwardly relative to the adjuster housing 122.

A sheath remover 125 is configured to mount to the front 101 of the injector device 100 (FIG. 1). The sheath remover 125 covers the grip surface 120 of the depth adjuster 117 when mounted to the front assembly 110 (e.g., see FIG. 8). The sheath remover 125 is configured to secure to the adjuster housing 122 without being rotationally fixed to the depth adjuster 117. Rotational movement of the sheath remover 125 does not cause rotational movement of the depth adjuster 117. Axial movement of the sheath remover 125 also does not cause axial movement of the depth adjuster 117. Rather, axial movement of the sheath remover 125 forward of the depth adjuster 117 removes the sheath remover 125 from the adjuster housing 122 (e.g., see FIG. 10). The sheath remover 125 is configured to remove a sheath 186 covering the needle 185 of the syringe 180 (see FIG. 10). Accordingly, the syringe 180 may be mounted to the front assembly 110 while the sheath 186 covers the needle 185 (see FIG. 8). The sheath remover 125 facilitates removing the sheath 186 without chancing a user's contact with the needle 185.

As shown in FIG. 9, the sheath remover 125 includes an outer wall 126 that is sized to fit around an exterior of the depth adjuster 117. Outer latch arms 127 extend rearwardly from the outer wall 126 and secure to the adjuster housing 122 (FIG. 9). The sheath remover 125 also includes an inner wall 128 that is sized to fit within the depth adjuster 117 and around the needle sheath 186 (see FIG. 9). Inner latch arms 129 extend rearwardly from the inner wall 128 to catch over edges of the needle sheath 186. The sheath remover 125 is removed from the front assembly 110 by pulling the sheath remover 125 forwardly of the front assembly 110 with sufficient force to unlatch the outer latch arms 127 (see FIG. 10). The inner latch arms 129 entrain and carry the needle sheath 186 as the sheath remover 125 is moved away from the front assembly 110 (see FIG. 10).

As shown in FIG. 3, the rear assembly 130 includes an outer housing arrangement 131, an injection assembly 140, an inner housing 150, and a trigger arrangement 170. In some implementations, the rear assembly 130 includes an interlock arrangement 160 that connects the rear assembly 130 to the front assembly 110 (e.g., see FIG. 15). The interlock arrangement 160 enables the injector device 100 to be configured between a disabled state (see FIGS. 13 and 15) in which the injection assembly 140 cannot be actuated and an enabled state (see FIGS. 14 and 16) in which the injection assembly 140 can be actuated as will be disclosed in more detail herein. In some implementations, the rear assembly 130 includes an indicator assembly 175 (FIG. 3) that provides a completion indicator as will be disclosed in more detail herein.

Figure 17:
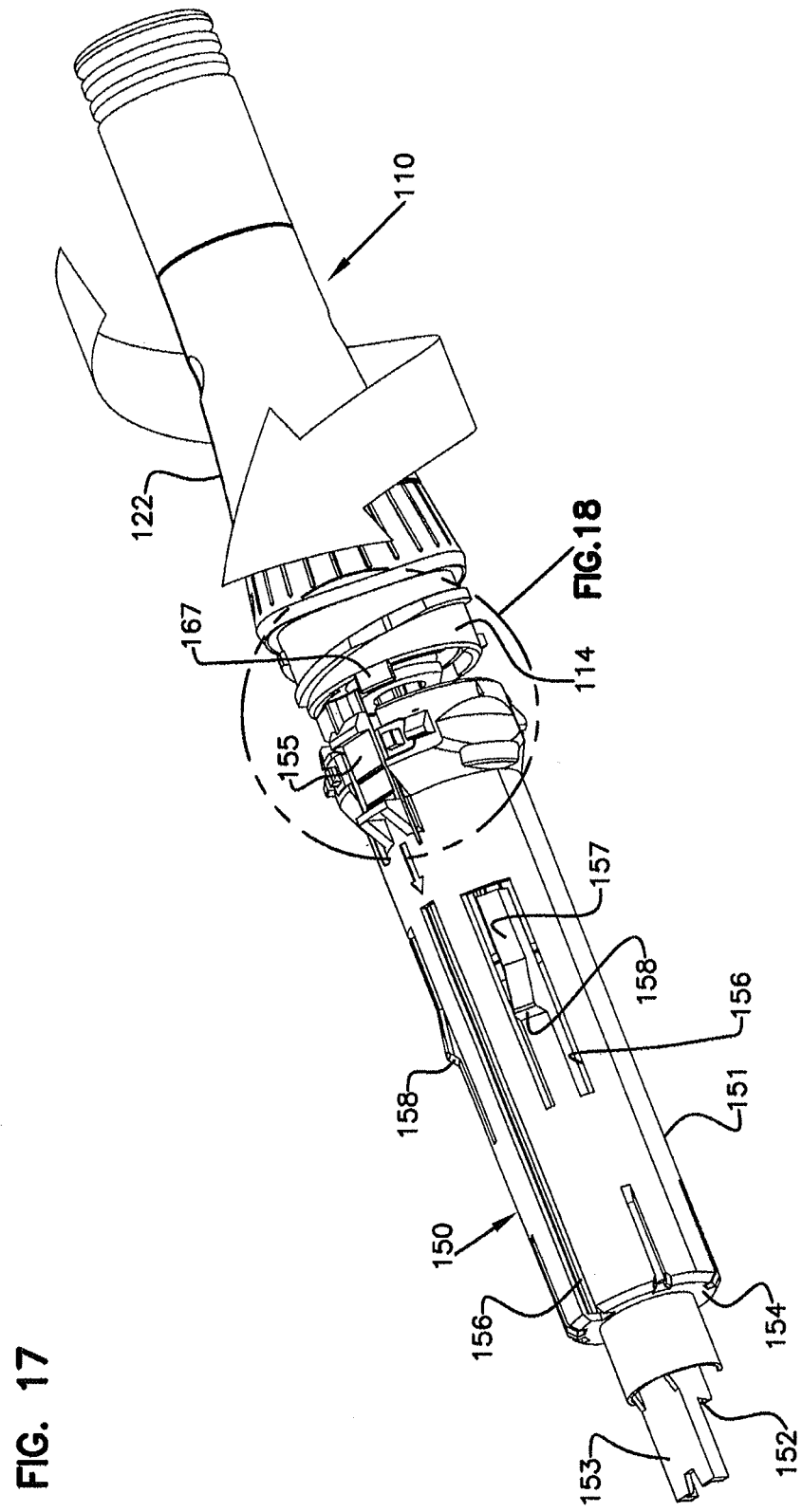
FIG. 17 is a perspective view of an inner housing of the rear assembly positioned relative to the front assembly shown in isolation from an outer housing of the rear assembly so that an interlock arm and rearwardly extending tab are visible.
Figure 21:
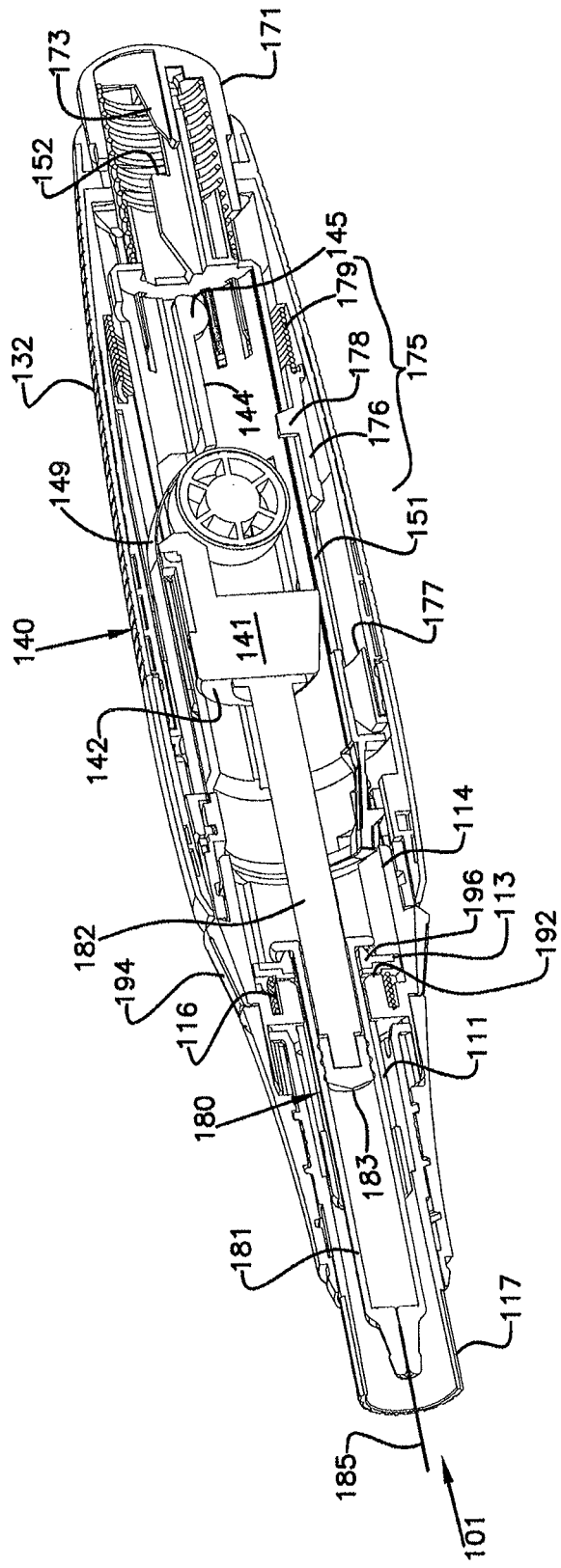
FIG. 21 is an axial cross-sectional view of the injector device of FIG. 16 with a trigger button depressed, a ram of the injection assembly released from a cocked position, and a syringe carrier bottomed out.

The inner housing 150 of the rear assembly 130 includes a hollow body 151 having an open end and a closed end (see FIGS. 12 and 17). The open end forms part of the interlock arrangement 160 (FIG. 12). The closed end is formed by a ceiling structure 154 from which a ledge arrangement 152 extends rearwardly (FIG. 17). The ledge arrangement 152 defines one or more rearward-facing shoulders positioned at a location spaced rearwardly from the ceiling structure 154 (FIGS. 17 and 21). In one example implementation, the ledge arrangement 152 includes two rearward-facing shoulders. A guide structure 153 extends rearwardly of the ledge arrangement 152 (FIGS. 12 and 17).

Still referring to FIG. 3, the injection assembly 140 includes a ram 141 and a constant force spring 149 that biases the ram 141 towards the front 101 of the injector device 100. At least part of the ram 141 is disposed within the inner housing 150 between the open end and the closed end. The ram 141 is configured to move (e.g., slide) within the inner housing 150 between at least a cocked position (FIG. 7) and a "bottomed out" position (FIG. 5). When in the cocked position, the ram 141 is located at the closed end of the inner housing 150. When in the bottomed out position, the ram 141 is located closer to the open end of the inner housing 150. In certain implementations, the ram 141 may be located forward of the inner housing 150 when in the bottomed out position.

The ram 141 defines an abutment surface 142 that faces towards the front 101 of the injector device 100 (FIG. 3). The abutment surface 142 is configured to contact and push a plunger 182 of the syringe 180 when moving towards the bottomed out position (see FIGS. 21 and 22). In one example implementation, the abutment surface 142 is flat (see FIG. 5). In some implementations, the abutment surface 142 is spaced from the plunger 182 when the ram 141 is in the cocked position (see FIGS. 15 and 16).

The ram 141 also includes a latch arm 144 that extends through a hole in the ceiling structure 154 to the ledge arrangement 152 (see FIG. 12). The latch arm 144 defines latching lugs 145 that are configured to seat on the rearward-facing shoulders of the ledge arrangement 152 to releasably secure the ram 141 to the ledge arrangement 152 in the cocked position (e.g., see FIG. 20). The lugs 145 of the latch arm 144 are configured to retain the ram 141 against the bias of the constant force spring 149 to maintain the ram 141 in the cocked position.

The ram 141 also defines a spring support section 143 (FIG. 3) at an intermediate position between the abutment surface 142 and the latch arm 144. In some implementations, a barrel 148 (FIG. 3) is mounted to the spring support section 143 and the constant force spring 149 is wrapped or otherwise mounted around the barrel 148 (e.g., see FIG. 12). An opposite end of the spring 149 is clamped, fastened, or otherwise secured between the inner housing 150 and the interlock arrangement 160 (see FIG. 12).

The outer housing arrangement 131 includes a rear outer housing 132 that receives the inner housing 150 (see FIG. 3). A trigger arrangement 170 is mounted to a rear end of the rear outer housing 132 (see FIG. 3). In some implementations, the trigger arrangement 170 includes a button 171 having forwardly extending latch arms 172 (FIGS. 3 and 20) that snap-fit or otherwise secure to internal shoulders defined by the rear outer housing 132 (e.g., see FIG. 7). The button 171 protrudes rearwardly from the rear outer housing 132 (e.g., see FIG. 7).

Figure 20:
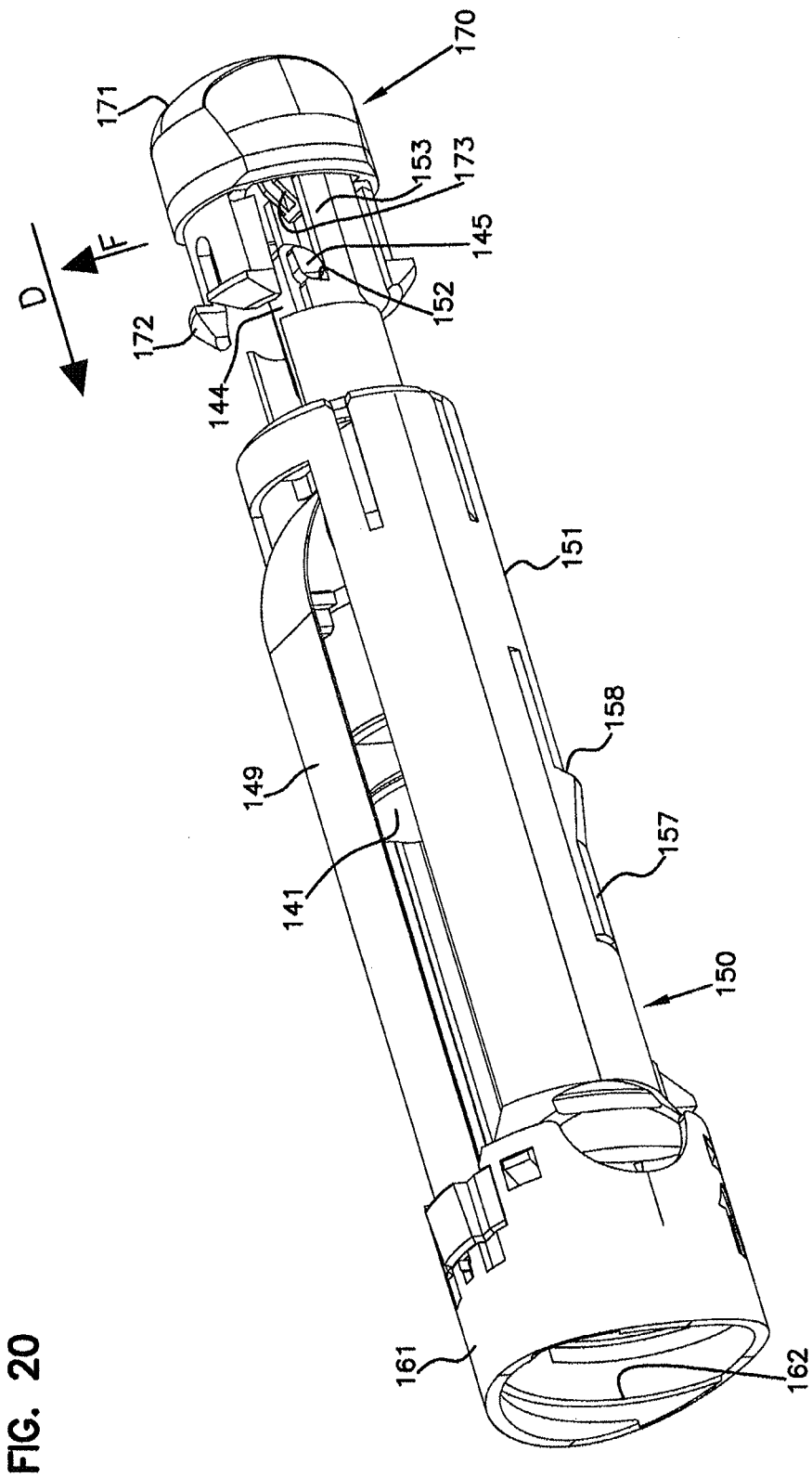
FIG. 20 is a perspective view of the trigger button disposed around a ledge structure of an inner housing.

The button 171 is moveable relative to the rear outer housing 132 between a ready position (e.g., see FIG. 5) and a depressed position (e.g., see FIG. 12). The button 171 is disposed further within the rear outer housing 132 when in the depressed position than when in the ready position. A trigger spring 174 biases the button 171 to the start position (see FIG. 5). A ramped structure 173 extends forwardly along the hollow interior of the button 171 (FIGS. 12 and 20). Moving the button 171 from the ready position to the depressed position against the bias of the trigger spring 174 causes the ramped structure 173 to move forwardly relative to the rear outer housing 132.

Figure 22:
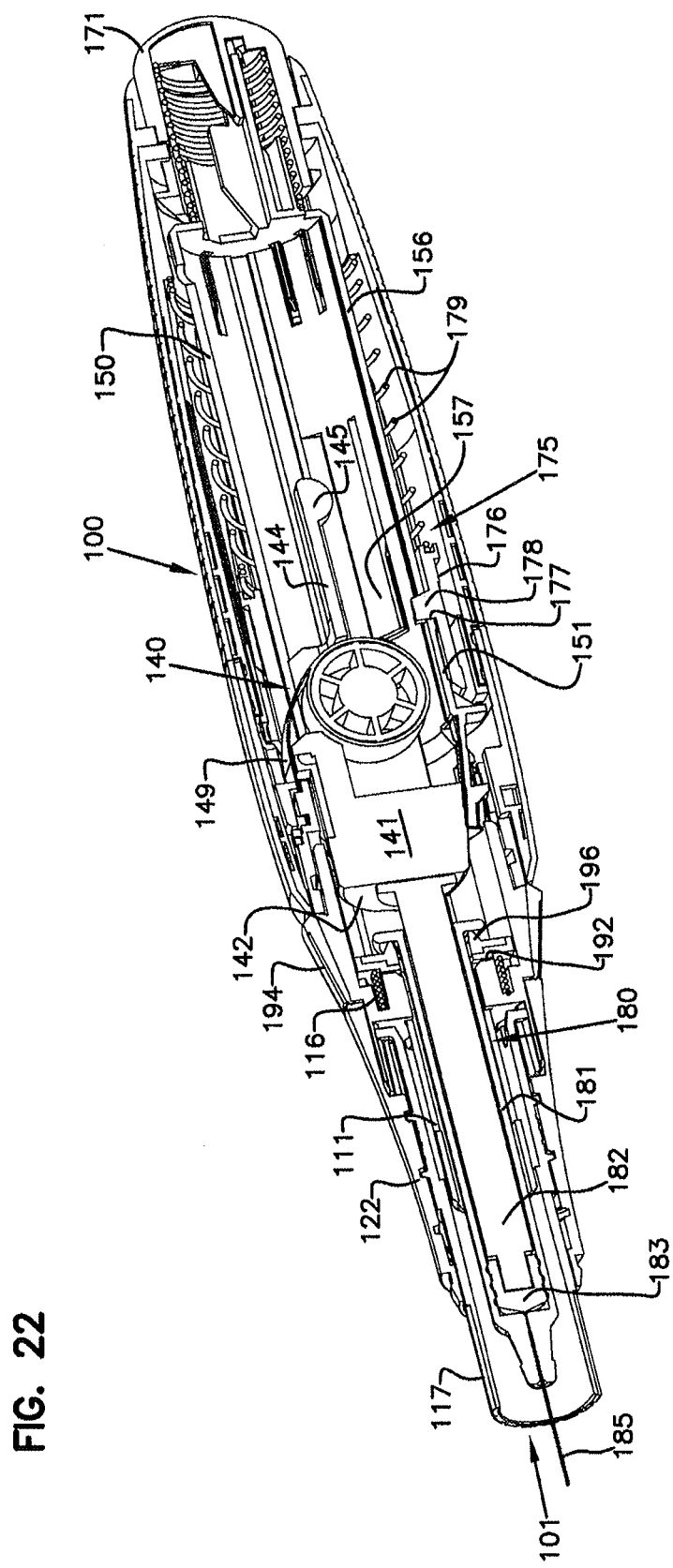
FIG. 22 is an axial cross-sectional view of the injector device of FIG. 21 with the plunger bottomed out in the syringe and a sudden completion indicator disposed in a forward position.

In some implementations, the indicator assembly 175 can be disposed between the inner housing 150 and the rear outer housing 132 (see FIGS. 3, 12, and 22). The indicator assembly 175 includes an indicator body 176 (FIG. 3). In some implementations, the indicator body 176 includes a colored surface. In other implementations, the indicator body 176 includes a surface on which indicia is printed. In some implementations, the indicator body 176 also includes a track follower 178 that extends radially inwardly from the body 176 to interact with the inner housing body 151 (see FIGS. 21 and 22).

The indicator body 176 is configured to slide along an exterior of the inner housing body 151 between a rearward (i.e., restrained) position (FIG. 21) and a forward (i.e., biased) position (FIG. 22). A biasing member (i.e., an indicator spring) 179 biases the indicator body 176 towards the forward position. In some implementations, one or more tracks 156 or cutouts extend longitudinally along the circumferential wall of the hollow body 151 of the inner housing 150 (FIG. 17). In certain implementations, the track follower 178 of the indicator body 176 extends into and is configured to slide along one of the tracks 156 to inhibit rotational movement of the indicator body 176 (FIG. 12). In some implementations, the track follower 178 can be utilized to reset the indicator member 176 during priming of the injection assembly 140 as will be disclosed in more detail herein.

The indicator body 176 is retained against the bias of the indicator spring 179 by stops 158 (FIGS. 17, and 20) provided on the inner housing 150. The stops 158 are disposed on one or more flexible arms 157 that extend within one or more of the cutouts in the hollow body 151 (see FIG. 17). In some implementations, the arms 157 are configured to flex radially inwardly towards the interior of the hollow body 151. The stop members 158 extend outwardly from the flexible arms 157. The indicator spring 179 is sufficiently strong to push the indicator body 176 over the stop members 158, thereby pressing the stop members 158 into the cutouts towards the interior of the inner housing 150 (see FIG. 22). However, when the ram 141 is disposed in the cocked position within the inner housing 150 (e.g., see FIG. 21), the ram 141 inhibits inward movement of the stop members 158 as will be described in more detail herein. Accordingly, the stop members 158 retain the indicator body 176 against the bias of the indicator spring 179 until the ram 141 is moved to the biased position.

Figure 23:
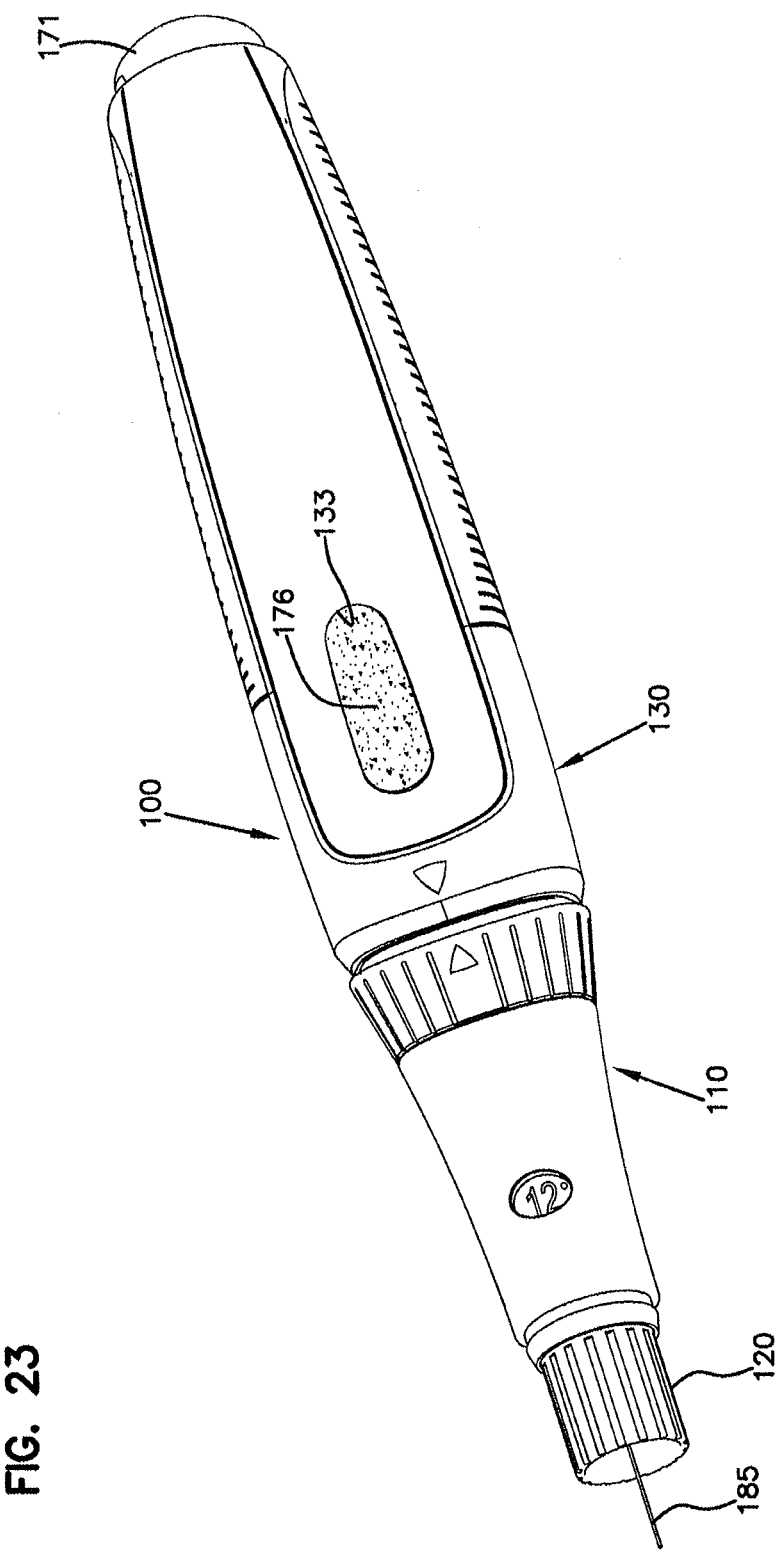
FIG. 23 is a perspective view of the injector device of FIG. 2 with a syringe needle protruding from a front of the injector device and a completion indicator disposed in the forward position.

The rear outer housing 132 defines at least one window aperture 133 (FIG. 3) through which the indicator body 176 is visible when the indicator body 176 is in the forward position (e.g., see FIG. 23). The indicator body 176 is not visible through the window aperture 133 when the indicator body 176 is in the rearward position (e.g., see FIG. 1). In one implementation, the rear housing 132 defines a window aperture 133 at only one of the side surfaces 103 of the housing 132. In another implementation, the rear housing 132 defines a window aperture 133 at both side surfaces 103 of the housing 132 and the indicator body 176 defines two indicator bodies 176. In certain implementations, a window arrangement 134 (FIG. 3) may be fixedly disposed within the rear outer housing 132 at the window aperture 133. The window arrangement 134 is formed of a translucent or semi-translucent material that fills the aperture 133 to protect the interior of the injector device 100.

The outer housing arrangement 131 also includes an intermediate outer housing 137 that fits together with the rear outer housing 132 (see FIG. 3). The intermediate outer housing 137 defines a support structure 138 that extends inwardly from an inner surface of the intermediate outer housing 137 (see FIG. 12). The support structure 138 defines a forward-facing shoulder 139 (FIG. 12).

In some implementations, one or both of the housings 132, 137 may include a grip surface 135, 137, respectively, to facilitate gripping of the injector device 100 (see FIG. 1). In some implementations, the grip surfaces 135, 137 extend over at least a portion of exterior surfaces of the housings 132, 137. In certain implementations, the grip surfaces 135, 137 are formed from compressible materials. In one example implementation, the grip surfaces 135, 137 are formed from rubber.

Figure 15:
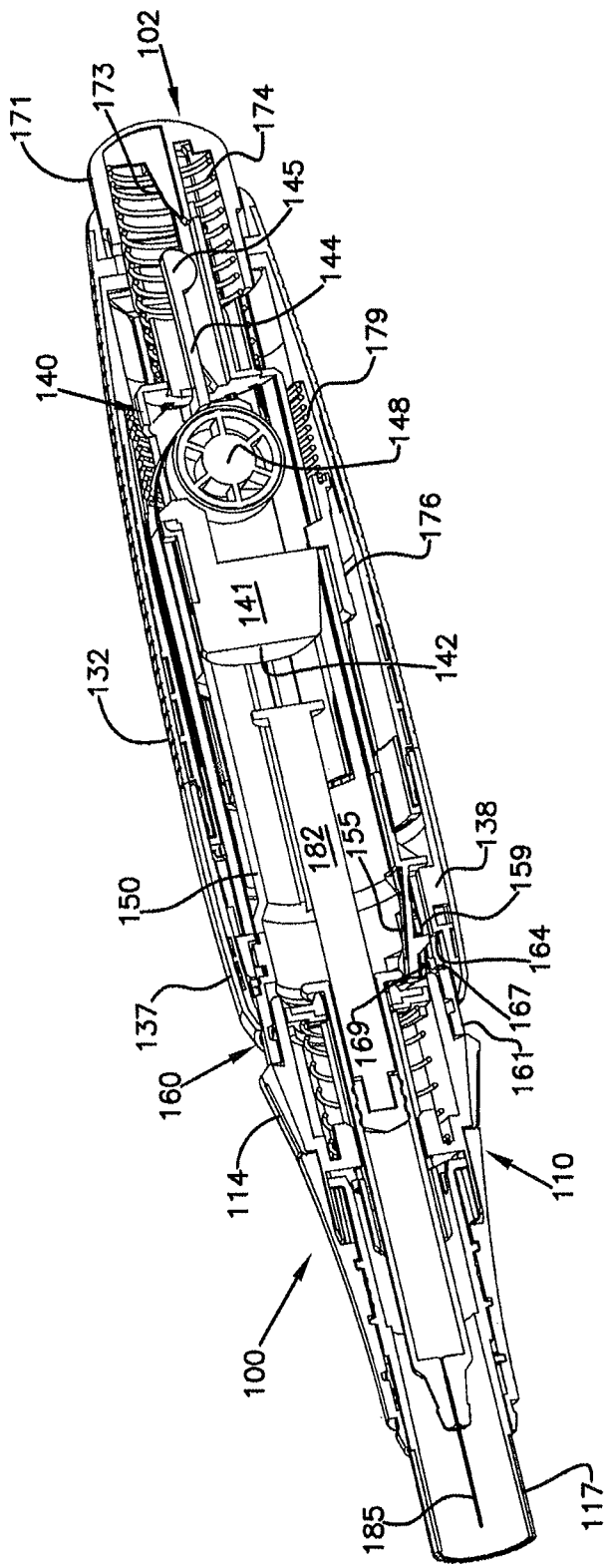
FIG. 15 is an axial cross-sectional view of the injector device of FIG. 13.

The interlock arrangement 160 couples the front assembly 110 to the rear assembly 130 (see FIG. 15). The interlock arrangement 160 includes an interlock body 161 defining an internal thread 162 at a forward end (FIGS. 3 and 12). The rearward end of the interlock body 161 is configured to attach to the inner housing 150 (FIG. 12). The internal thread 162 is sized to engage with an external thread 163 disposed on the carrier support 114 (see FIG. 11) to releasably couple the rear assembly 130 to the front assembly 110.

In some implementations, the internal thread 162 and external thread 163 are configured to facilitate fast threading the front and rear assemblies 110, 130. For example, in certain implementations, each of the internal thread 162 and the external thread 163 extends around an inner circumference of the respective assembly 110, 130 no more than twice (see FIGS. 11 and 12). In certain implementations, each of the internal thread 162 and the external thread 163 extends around the inner circumference more than once and less than twice. In certain implementations, each of the internal thread 162 and the external thread 163 extends no more than once around an inner circumference of the respective assembly 110, 130. In certain implementations, each of the internal and external threads 162, 163 extend around about half of the inner circumference of the respective assembly 110, 130.

As shown in FIG. 12, the inner housing 150 is configured to releasably lock to the intermediate outer housing 137. The inner housing 150 defines an interlock arm 155 extending forwardly of a fixed shoulder 164. The interlock arm 155 includes a flexible arm that is configured to be deflected inwardly relative to the rest of the inner housing 150 (see FIG. 15). The interlock arm 155 includes a latching hook extending radially outwardly from the arm 155 to define a rearward-facing shoulder 159 (FIG. 12). A free end of the interlock arm 155 defines a ramped or contoured surface 169 that tapers or curves laterally across the arm 155 (see FIGS. 18 and 19).

When the rear outer housing 132 and intermediate outer housing 137 are mounted over the inner housing 150, the support member 138 of the intermediate housing 137 is disposed between the fixed shoulder 164 of the inner housing 150 and the rearward-facing shoulder 159 of the latching hook (FIG. 12). Accordingly, the outer housing assembly 131 is held stationary relative to the inner housing 150 and interlock body 161. A portion of the interlock body 161 (e.g., a band) extends between the front assembly 110 and the rear assembly 130 (see FIG. 13).

FIGS. 4-7 illustrate how the injector device 100 is armed (i.e., how the ram 141 (FIG. 3) is moved from the bottomed out position to the cocked position). As shown in FIG. 4, the front assembly 110 is removed from the rear assembly 130 (e.g., by unthreading the carrier support 114 from the interlock body 161). As shown in FIG. 5, the front assembly 110 is flipped around so that the sheath remover 125 faces the rear assembly 130. As shown in FIGS. 6 and 7, the front end of the front assembly 110 is inserted into the rear assembly 130 and slid rearwardly within the inner housing 150.

The front end of the front assembly 110 engages the ram 141 and pushes the ram 141 rearwardly within the inner housing 150 towards the ceiling structure 154 (see FIG. 6). For example, in some implementations, the sheath remover 125 is pressed against the abutment surface 142 of the ram 141. In other implementations, depth adjuster 117 is pressed against the abutment surface 142. The ram 141 is moved rearwardly against the bias of the constant force spring 149. The ceiling structure 154 prevents the ram 141 from being moved too far rearward. As the ram 141 moves rearwardly, the latch arm 144 moves past the ceiling structure 154 towards the ledge arrangement 152 until the latch lugs 145 seat on the rearward shoulders of the ledge arrangement 152 in the cocked position (see FIG. 20).

FIGS. 8-11 illustrate mounting a syringe 180 into the front assembly 110. The syringe 180 includes an ampoule 181 configured to hold medicament. A plunger 182 extends through a rear end of the ampoule 181 to a piston or bung 183 that seals the medicament in the ampoule 181. A needle 185 (FIG. 10) couples to a needle hub 184 at a front end of the ampoule 181. A sheath 186 surrounds the needle 185 (e.g., see FIG. 9). The sheath 186 inhibits a person handling the syringe from being accidentally stuck or pricked by the needle 185.

As shown in FIG. 8, the syringe 180 is inserted into the rear end of the front assembly 110. The sheathed end of the syringe 180 is inserted through the syringe carrier 111 so that the support section 112 of the carrier 111 surrounds a portion of the ampoule 181 (e.g., see FIGS. 9 and 10). The syringe 180 is inserted sufficiently far into the front assembly 110 such that the needle sheath 186 extends within the inner walls 128 of the sheath remover 125. The latch arms 129 of the inner walls 128 hook or otherwise secure over ends of the sheath 186 (see FIG. 9).

Figure 10:
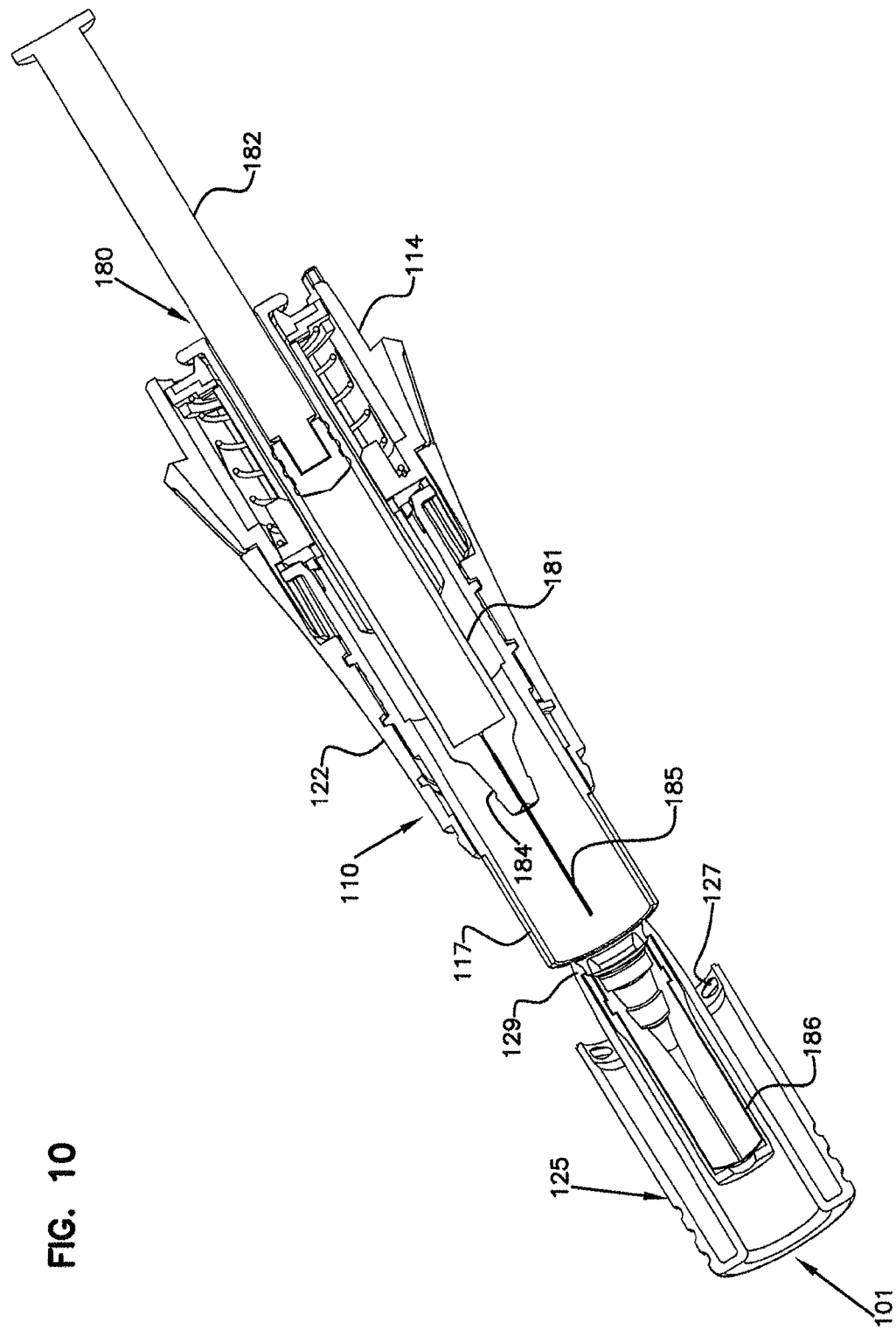
FIG. 10 shows the sheath remover and needle sheath being removed from the injector device of FIG. 9.
Figure 11:
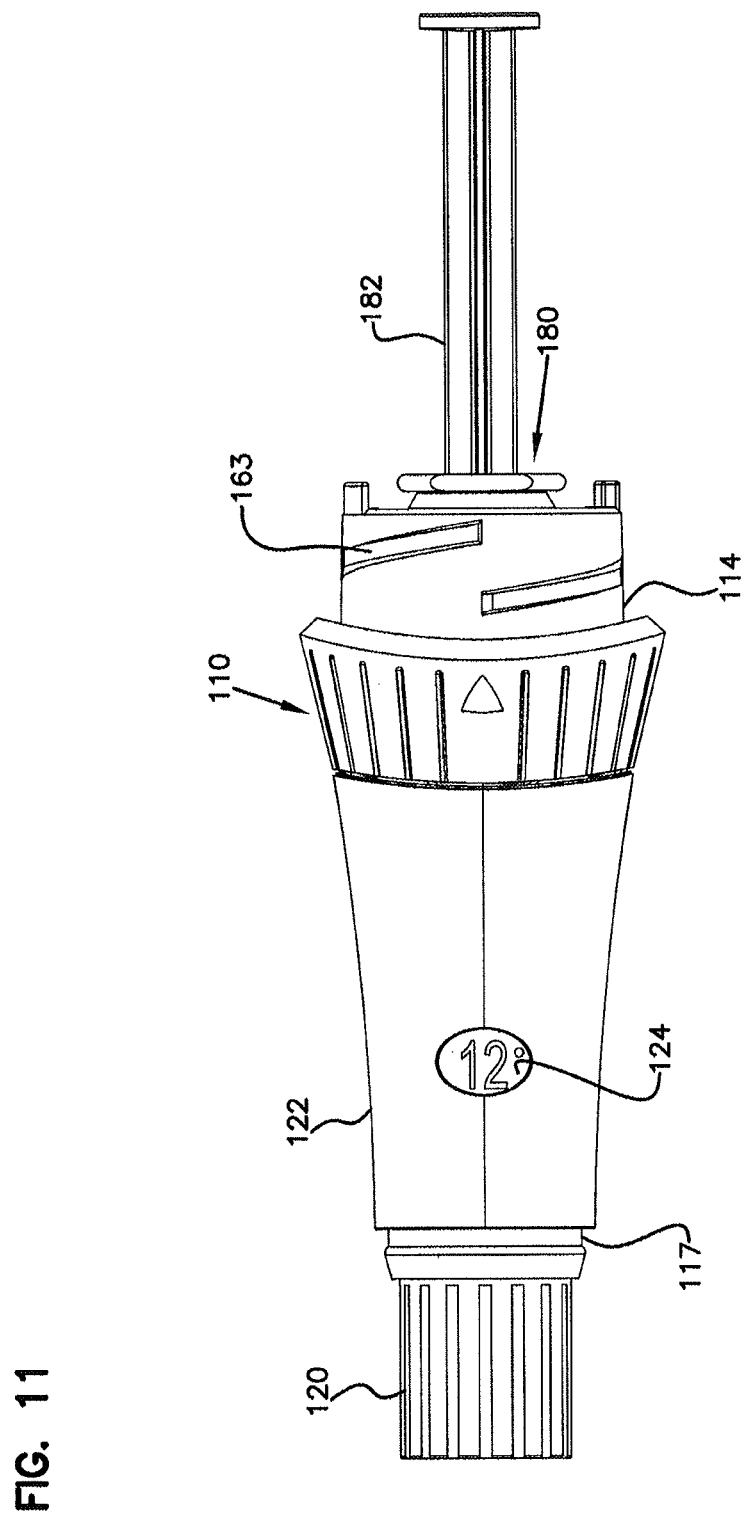
FIG. 11 is a side elevational view of the front assembly of FIG. 10 having a syringe loaded therein and the sheath remover removed.

As shown in FIG. 10, the sheath remover 125 entrains the sheath 186 when the sheath remover 125 is pulled forwardly of the front assembly 110, thereby removing the sheath 186 from the needle 185. As shown in FIG. 11, the grip surface 120 of the depth adjuster 117 is accessible when the sheath remover 125 is removed. The plunger 182 extends rearwardly of the ampoule 181 and the front assembly 110 when the syringe is mounted to the syringe carrier 111.

FIG. 12 illustrates a cross-section of the rear assembly 130 after the injection assembly 140 is armed and the injector device 100 is in a disabled configuration. While in the disabled configuration, actuation of the trigger 170 will not fire the injection assembly 140. The ram 141 is disposed in the cocked position and the latching lugs 145 of the ram 141 are seated on the ledge arrangement 152 of the inner housing body 151. The constant force spring 149 is tensioned.

The indicator body 176 is held in the restrained position against the bias of the indicator spring 179. In particular, the ram 141 inhibits the flexible arms 157 of the inner housing 150 from flexing inwardly, which enables the stops 158 (FIG. 18) to retain the indicator body 176. Furthermore, a shoulder 147 of the ram 141 may engage the track follower 178 to inhibit forward movement of the indicator body 176 (FIG. 12). The shoulder 147 also can push against the track follower 178 when arming the injection device 140 to reset the indicator body 176 in the rearward position (e.g., see FIGS. 5 and 7).

While the injector device 100 is disabled, the inner housing body 151 is axially fixed relative to the outer housing assembly 131 (see FIG. 12). A fixed shoulder 164 of the inner housing body 151 seats against one end of the support member 138 of the intermediate outer housing 137, thereby inhibiting forward axial movement of the inner housing 150 relative to the rear outer housing 132. The latching hook (i.e., the rearward-facing shoulder 159) of the interlock arm 155 engages a shoulder 139 at an opposite end of the support member 138, thereby inhibiting forward axial movement of the rear outer housing 132 relative to the inner housing 150 (FIG. 12). In addition, the trigger spring 174 biases the rear outer housing 132 into an extended position relative to the inner housing 150 (FIG. 12). For example, one end of the spring 179 seats on the ceiling structure 154 of the inner housing 150 and the opposite end of the spring 179 presses against an interior of the button 171 (see FIG. 12).

As shown in FIG. 12, depressing the trigger button 171 while the rear outer housing 132 is disposed in the extended position does not actuate the injection assembly 140. Pressing the trigger button 171 into the rear outer housing 132 causes the ramped structure 173 at the interior of the button 171 to move forwardly towards the ledge structure 152 of the inner housing 150. However, even when the button 171 is fully depressed, the ramped structure 173 does not reach the latching lugs 145 of the ram latching arm 144. Accordingly, the button ramped structure 173 cannot unlatch the latch arm 144 from the ledge structure 152 to actuate the injection assembly 140.

FIGS. 13-19 illustrate how the injector device 100 is transitioned from the disabled configuration to the enabled configuration. As shown in FIG. 13, the front assembly 110 is attached to the rear assembly 130 so that a band of the interlock body 161 is visible between the carrier support 114 and the intermediate outer housing 137. A first alignment indicator 165 of the front assembly 110 aligns with a second alignment indicator 166 of the rear assembly 130. For example, the front assembly 110 maybe screwed into the rear assembly 130 until the first and second alignment indicators 165, 166 point to each other to indicate rotational alignment of the front and rear assemblies 110, 130. As shown in FIG. 14, when the front and rear assemblies 110, 130 are rotationally aligned, the rear assembly 130 may be axially moved forwardly towards the front assembly 110 so that the intermediate outer housing 137 covers the interlock body 161 that was visible (compare FIGS. 13 and 14).

Figure 16:
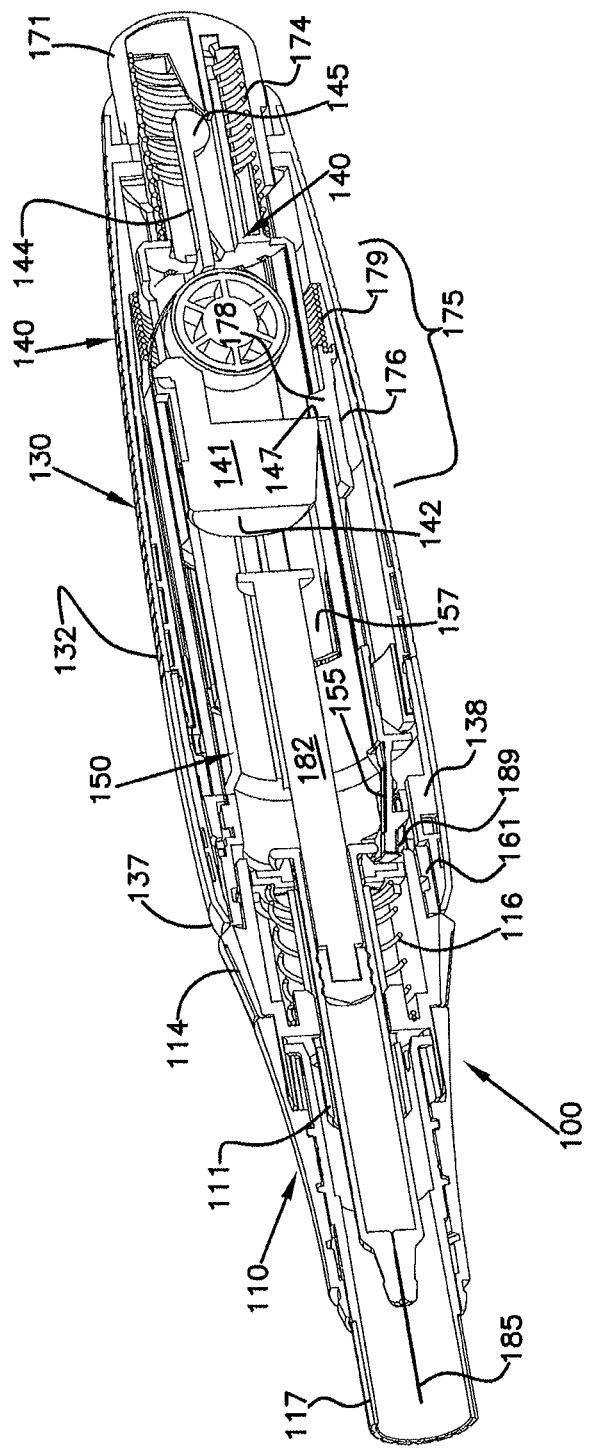
FIG. 16 is an axial cross-sectional view of the injector device of FIG. 14.

FIGS. 15 and 16 are axial cross-sectional views of the injector device 100 showing the transition from the disabled configuration to the enabled configuration. When in the disabled configuration, the axial spacing between the ledge structure 152 of the inner housing 150 and the rear end 102 of the rear outer housing 132 is sufficient to maintain separation of the ramped structure 173 of the trigger button 171 from the latch lugs 145 of the ram 141 even when the trigger button 171 is depressed (e.g., see FIG. 15). Accordingly, depressing the trigger button 171 when the injector device 100 is in the disabled configuration does not actuate the injection assembly 140.

Since the latching arm 155 is unlocked (i.e., flexed inwardly), the rear outer housing 132 can be moved relative to the inner housing 150 and the front assembly 110 to a forward, retracted position against the bias of the trigger spring 174. The rear outer housing 132 moves to cover the interlock body 161 so that the interlock body 161 is no longer visible to a user. As shown in FIG. 16, sliding the rear outer housing 132 to the retracted position brings the trigger button 171 closer to the ledge structure 152 and ram latching lugs 145. Depressing the trigger button 171 of the now enabled injector device 100 moves the ramped structure 173 into engagement with the latching lugs 145 of the ram latch arm 144.

Figure 18:
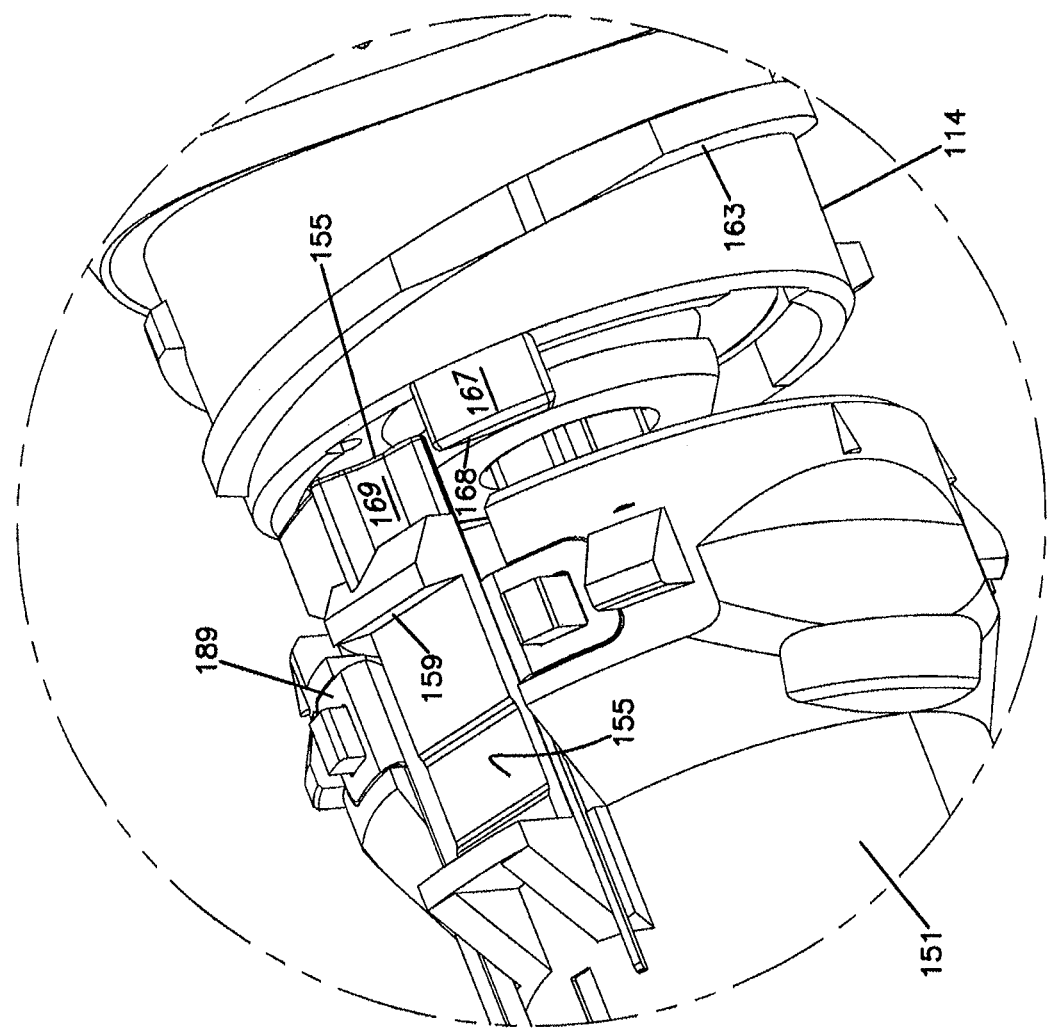
FIG. 18 is an enlarged perspective view of a portion of FIG. 17.
Figure 19:
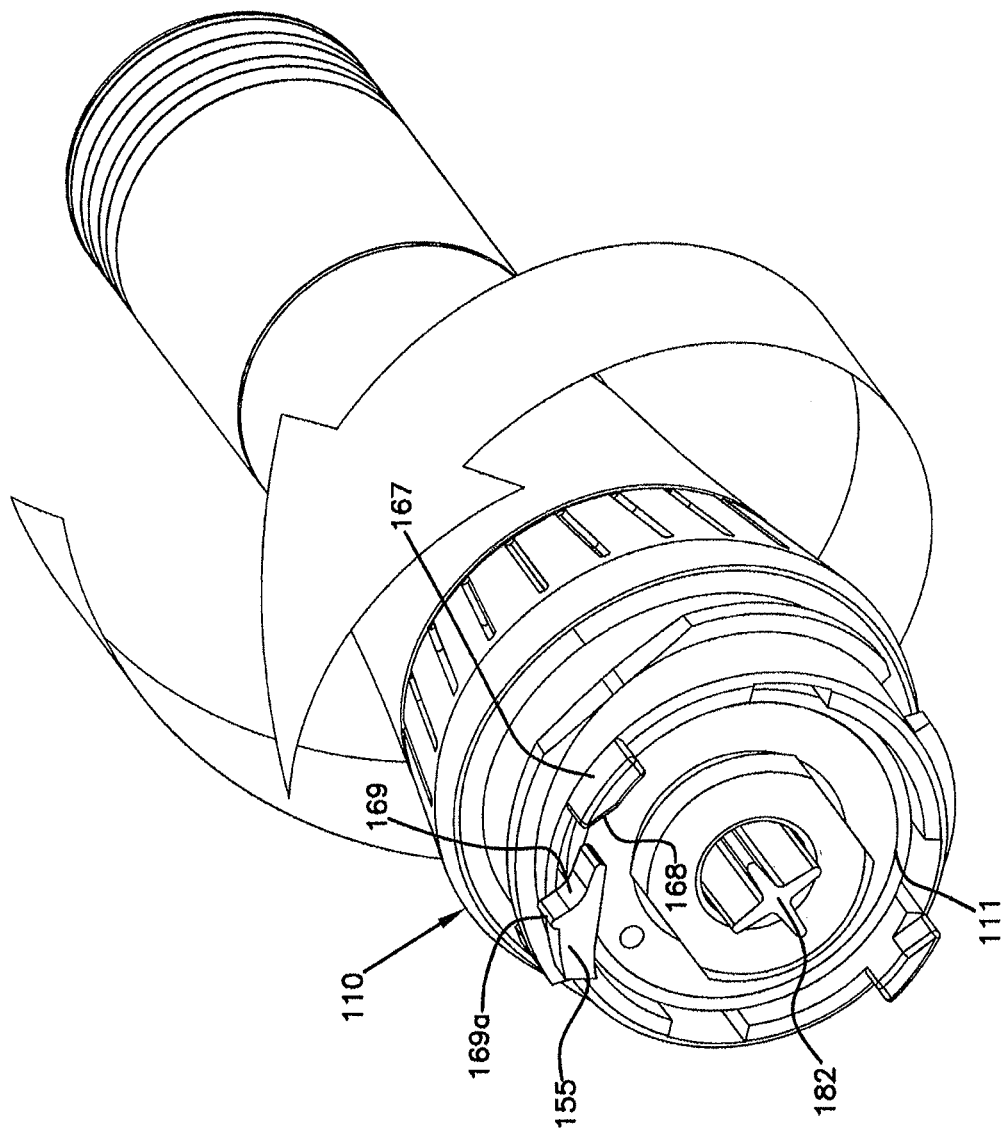
FIG. 19 is a rear perspective view of the front assembly of FIG. 16 with a lateral cross-section of the interlock arm visible.

FIGS. 17-19 illustrate how the interlock arrangement 160 enables transitioning of the injector device 100 from the disabled configuration to the enabled configuration. As shown in FIG. 17, the front assembly 110 includes one or more rearwardly extending tabs 167 (e.g., disposed at a rear of the carrier support 114). As shown in FIG. 19, the rearwardly extending tab 167 defines a ramped or otherwise contoured surface 168 that is shaped to interact with a ramped or otherwise contoured surface 169 at the free end of the interlock arm 155 of the inner housing 150. For example, the tab 167 may ride over a snap-over surface 169a of the contoured surface 169. In certain implementations, the tab 167 makes an audible sound (e.g., a click) when the tab 167 rides over the snap-over surface 169a.

When the front assembly 110 is threadably coupled to the rear assembly 130, the rearwardly extending tab 167 of the front assembly 110 engages the free end of the interlock arm 155 to deflect the interlock arm 155 radially inwardly as shown in FIG. 15. Flexing the interlock arm 155 inwardly moves the latching hook (and hence the rearward-facing shoulder 159) of the interlock arm 155 away from the support member 138 of the inner housing 150 (see FIG. 15). The rear outer housing assembly 132 can be moved forwardly relative to the interlock body 161 while the interlock arm 155 is retained at the inwardly flexed position (see FIG. 16).

In some implementations, the interlock assembly 160 includes a latch spring 189 (FIG. 3) that biases the interlock arm 155 radially outwardly in the locking position. In some implementations, the latch spring 189 provides support for the interlock arm 155 to inhibit breaking of the arm 155 after repeated use. In such implementations, the interlock arm 155 is primarily biased towards the locking position by material resiliency and elasticity of the interlock arm 155, itself. In other implementations, the latch spring 189 functions to maintain the interlock arm 155 in the locking position.

FIGS. 16 and 20-22 illustrate the actuation of the injection assembly 140 of the injector device 100. As shown in FIG. 16, the injector device 100 is arranged in the enabled configuration in order to initiate injection. The carrier spring 116 biases the syringe carrier 111 rearwardly so that the needle 185 is disposed within the depth adjuster 117. The syringe plunger 182 extends rearwardly towards the ram 141, which is disposed in the cocked position. In certain implementations, the abutment surface 142 of the ram 141 is axially spaced from the syringe plunger 182. In other implementations, the ram 141 abuts the syringe plunger 182. The trigger button 171 is within reach of the latching lugs 145 of the ram latch arm 144.

As shown in FIG. 20, depressing the trigger button 171 in a depression direction D causes the ramped structure 173 to push the latching lugs 145 of the ram latch arm 144 in a flex direction F away from the ledge structure 152 of the inner housing 150. In certain implementations, the ledge structure 152 is contoured so that moving the latching lugs 145 in a lateral flex direction F causes the ram 141 to move rearwardly against the bias of the constant force spring 149 until the latching lugs 145 clear the ledge structure 152 (see FIG. 20). When the latching lugs 145 clear the ledge structure 152, the ram 141 is no longer retained against the bias of the constant force spring 149.

As shown in FIG. 21, the constant force spring 149 pulls the ram 141 forwardly towards the biased position when the ram 141 is no longer retained in the cocked position. As the ram 141 moves forwardly, the abutment surface 142 of the ram 141 engages the syringe plunger 182. However, the ram 141 does not immediately move the plunger 182 within the ampoule 181. Rather, a compression resistance of the carrier spring 116 is sufficiently low that the carrier spring 116 begins to compress before the plunger 182 begins moving within the ampoule 181. As the carrier spring 116 compresses, the syringe carrier 111 moves forwardly relative to the carrier support 114 until a hub 113 of the syringe carrier 111 engages a forward wall of the carrier support 114 (e.g., engages the first damper 192). The syringe carrier 111 carries the syringe 180 forward, thereby injecting the needle 185 into the injection site.

As shown in FIG. 22, the ram 141 depresses the plunger 182 within the ampoule 181 to dispense the medicament. When the syringe carrier 111 bottoms out (i.e., engages the forward wall), the forward force of the ram 141 is sufficient to overcome the resistance of the plunger 182. Because the ram spring 149 is a constant force spring, the medicament is dispensed form the syringe 180 at a more consistent rate than with a coil spring. After the medicament is dispensed, the ram spring 149 maintains forward pressure on the syringe plunger 182. Accordingly, the syringe needle 185 remains extending from the front end 101 of the injector device 100, even after the injector device 100 is removed from the injection site.

Referring to FIGS. 16, 21, and 22, the sudden completion indicator 175 is automatically actuated by the injection assembly 140. As shown in FIG. 16, the indicator body 176 is disposed the rearward position against the bias of the indicator spring 179 before actuation of the trigger button 171. While in the cocked position, the ram 141 inhibits inwardly flexing of the arms 157 of the inner housing 150. Accordingly, stop members 158 (FIG. 20) hold the indicator body 176 against the bias of the spring 179. Further, the shoulder 147 of the ram 141 engages the track follower 178 of the indicator body 176 (FIG. 16). As shown in FIG. 21, the indicator body 176 is still retained in the rearward position because the ram 141 still extends along a portion of the flexible arms 157.

As shown in FIG. 22, the indicator body 176 is biased over the stop members 158 when the ram 141 moves sufficiently forwardly within the inner housing 150 to clear the flexible arms 157 to enable inward movement of the stop members 158. In the example shown, the ram 141 clears the flexible arms 157 when the piston 183 bottoms out in the syringe ampoule 181. In other implementations, the ram 141 clears the flexible arms 157 when the plunger 182 has moved sufficiently forward to dispense a dose of medicament from the syringe 180 (e.g., even if the piston 183 is not fully "bottomed out").

The indicator spring 179 pushes the indicator body 176 forward over the inner housing 150. As the housing 176 slides forward, the track follower 178 slides within a longitudinal track 156 defined in the sidewall of the inner housing body 151. The track follower 178 inhibits rotation of the indicator member 176 as the indicator member 176 moves forward. Accordingly, the track follower 178 inhibits the indicator body 176 from moving out of circumferential alignment with the window 134 (FIG. 1).

As shown in FIG. 22, the indicator body 176 radially aligns with the window 134 when the medicament is dispensed. As shown in FIG. 1, the inner housing body 151 is visible through the window 134 before the indicator body 176 aligns with the window 134. As shown in FIG. 22, the indicator body 176 is visible through the window 124 when the dispensation is complete. In some implementations, the indicator body 176 is a different color (e.g., red) than the inner housing body 151 (e.g., white). Accordingly, the sudden color change in the window 134 indicates completion of the injection process.

As noted above, the phrase "at completion" can refer to the timeframe including the moment of completion, a time immediately after the moment of completion, or a time within a few milliseconds before or after completion (e.g., due to tolerance within the injector device). When multiple events occur "at completion," the events may occur simultaneously, one immediately following the other, or within a few milliseconds within each other. In some implementations, the track follower 178 creates an audible noise (e.g., a "click") when the track follower 178 engages a shoulder 177 of the inner housing 150 when the indicator body 176 reaches the forward position (see FIG. 22). Accordingly, in some implementations, the sudden completion indicator 175 makes an audible noise to signal completion of the dispensation step.

In some implementations, the indicator spring 179 is sufficiently strong that the indicator body 176 appears to instantaneously fill the window 134. For example, the indicator spring 179 may move the indicator body 176 forward so quickly that a user could not follow the movement of the front end of the indicator body 176 along the window 134. In certain implementations, the movement of the indicator body 176 relative to the window 134 is not tied to (i.e., is isolated from) the movement of the plunger 182 within the syringe ampoule 181. For example, once clear of the flexible arms 157, the indicator body 176 moves forwardly by the indicator spring 179 without being influenced by the position of the ram 141 within the inner housing body 151.

The above injector device 100 is configured for use with a syringe containing an injectable fluid. One example fluid suitable for inclusion in the syringe is Glatiramer acetate. Glatiramer acetate (GA), also known as Copolymer-1, has been shown to be effective in treating multiple sclerosis (MS) (Lampert, 1978). Daily subcutaneous injections of glatiramer acetate (20 mg/injection) reduce relapse rates, progression of disability, appearance of new lesions by magnetic resonance imaging (MRI), (Johnson, 1995) and appearance of "black holes" (Filippi, 2001).

COPAXONE® is the brand name for a formulation containing glatiramer acetate as the active ingredient. Glatiramer acetate is approved for reducing the frequency of relapses in relapsing-remitting multiple sclerosis (RRMS). Glatiramer acetate consists of the acetate salts of synthetic polypeptides containing four naturally occurring amino acids: L-glutamic acid, L-alanine, L-tyrosine, and L-lysine with an average molar fraction in COPAXONE® of 0.141, 0.427, 0.095 and 0.338, respectively. In COPAXONE®, the average molecular weight of the glatiramer acetate is 4,700-11,000 daltons. Chemically, glatiramer acetate is designated L-glutamic acid polymer with L-alanine, L-lysine and L-tyrosine, acetate (salt). Its structural formula is:

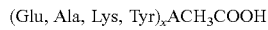

(Glu, Ala, Lys, Tyr)$_x$·ACH$_3$COOH

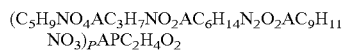

$(C_5H_9NO_4AC_3H_7NO_2AC_6H_{14}N_2O_2AC_9H_{11}NO_3)_p$·$APC_2H_4O_2$

CAS-147245-92-9.

The recommended dosing schedule of COPAXONE® for relapsing-remitting multiple sclerosis is 20 mg per day injected subcutaneously (Physician's Desk Reference). Additional information about dosing schedules also can be found in U.S. Pat. Nos. 3,849,550; 5,800,808; 5,858,964; 5,981,589; 6,048,898; 6,054,430; 6,214,791; 6,342,476; and 6,362,161, the disclosures of are hereby incorporated by reference herein.

Although its mechanism of action is not completely elucidated, GA is thought to bind to and to be displayed as an antigen within the groove of a major histocompatibility complex (MHC) molecule. Alternatively, GA is thought to be engulfed by antigen presenting cells (APC) and fragments are then presented. Either way, the presentation of GA leads to the generation of GA-specific T cells. Through mechanisms that are still unclear, the GA-specific T cells are predominantly T helper 2 (Th2) biased. Th2 cells produce Th2 cytokines which inhibit the production of cytokines by Th1 cells or macrophages, and tend to be anti-inflammatory. Unlike interferon-β which apparently has potent activity at the blood-brain barrier (BBB) and impairs the trafficking of inflammatory cells into the CNS, GA has negligible effect at the BBB, allowing GA-specific Th2 lymphocytes to enter the CNS to decrease inflammation through bystander suppression (Yong, 2002).

Some aspects of the injector device include (a) an injector body including a front assembly and a rear assembly that cooperate to define an interior; (b) a syringe configured to be coupled to the syringe carrier for movement therewith; and (c) an injection assembly disposed within the interior of the injector body. The front assembly includes a forward housing, a syringe carrier that is movable relative to the forward housing between a rearward position and a forward position. A first damper is disposed at a rearward face of the forward housing, and a second damper disposed at a rear of the syringe carrier, wherein the syringe carrier engages the first damper when in the forward position and the syringe carrier is spaced from the first damper when in the rearward position. The syringe includes an ampoule, a needle, and a plunger. The needle extends from a first end of the ampoule, and the plunger extends from a second end of the ampoule. At least a portion of the ampoule engages the second damper. The ampoule is configured to hold a common volume of either one of at least two different medicament formulations without modification to the injector device. A first of the two different medicament formulations has a first viscosity and a second of the two different medicament formulations has a second viscosity that is different from the first viscosity. The injection assembly is configured to dispense the medicament formulation held by the syringe. The injection assembly includes a ram driven by a constant force spring, wherein releasing the constant force spring drives the syringe carrier from the rearward position to the forward position until the syringe carrier engages the first damper and wherein the constant force spring drives the plunger within the ampoule of the syringe after the syringe carrier is in the forward position. The first and second dampers cooperate to inhibit breaking of the ampoule during movement of the syringe carrier and movement of the plunger.

In certain example implementations, the first damper is formed from an over-molded section that also extends along an exterior of the injector body.

In certain example implementations, the over-molded section includes a compressible grip surface extending over a portion of an exterior of the injector body.

In certain example implementations, each of the medicament formulations comprises Glatiramer acetate. In one example implementation, the first medicament formulation is a 1 ML of solution comprising 20 mg of Glatiramer acetate and the second medicament formulation is a 1 ML of solution comprising 40 mg of Glatiramer acetate.

In certain example implementations, the ram is retained against a bias of the constant force spring until a trigger member is actuated to release the constant force spring.

In certain example implementations, the trigger member includes a button that is actuated by pushing the button at least partly into the injector body.

In certain example implementations, the needle is configured to extend from the injector body when the syringe carrier is disposed in the forward position and wherein the injector body includes a depth adjuster that changes a length of the needle that extends from the injector body.

In certain example implementations, the depth adjuster is movable between discrete stop positions, each discrete stop position corresponding to a different needle depth so that moving the depth adjuster to one of the discrete stop positions selects the corresponding needle depth.

In certain example implementations, a needle sheath remover fits over the depth adjuster and is configured to couple to the depth adjuster so that the depth adjuster remains axially and rotationally fixed during any movement of the needle sheath remover.

In certain example implementations, digits are displayed at the depth adjuster to indicate a needle depth, wherein the displayed digits are at least 4 mm in size.

In certain example implementations, each of the front and rear housing assemblies includes a threaded region that secures to the other threaded region to couple the front and rear housing assemblies together.

In certain example implementations, each of the threaded regions includes a thread that extends around no more than an inner circumference of the injector body.

In certain example implementations, the thread of each threaded region extends around about half of the inner circumference of the injector body.

In certain example implementations, the front housing assembly of the injector body includes a first tab and the rear housing assembly of the injector body defines a snap-over surface, wherein the first tab rides over the snap-over surface when the first and second housing assemblies are threaded together, and wherein the first tab makes an audible sound when the first tab rides over the snap-over surface.

In certain example implementations, a sudden completion indicator member is disposed within the interior of the injector body. The sudden completion indicator member is configured to move relative to the injector body between a first position and a second position. The sudden completion indicator member is not visible through a window defined in the injector body when in the first position and is visible through the window when in the second position, wherein movement of the sudden completion indicator member from the first position to the second position is actuated at completion of a dispensation step.

In certain example implementations, a color change is visible through the window when the sudden completion indicator member moves from the first position to the second position.

In certain example implementations, the injector device produces an audible sound at completion of the dispensation step.

In certain example implementations, the sudden completion indicator member is biased towards the second position by a biasing member; and wherein the injection assembly includes at least one stop member that retains the sudden completion indicator member against the bias of the biasing member, the stop member automatically releasing the indicator member at completion of the dispensation step.

The above specification, examples and data provide a complete description of the manufacture and use of the invention. Since many embodiments of the invention can be made without departing from the spirit and scope of the invention, the invention resides in the claims hereinafter appended.

REFERENCES

1. Lampert, Autoimmune and virus-induced demyelinating diseases. A review, *Am. J. Path.*, 1978, 91:176-208.
2. Johnson et al., Copolymer 1 reduces relapse rate and improves disability in relapsing-remitting multiple sclerosis: results of a phase III multicenter, double-blind placebo-controlled trial. The Copolymer 1 Multiple Sclerosis Study Group, *Neurol.*, 1995, 45:1268.
3. Filippi et al., Glatiramer acetate reduces the proportion of MS lesions evolving into black holes, *Neurol.*, 2001, 57:731-733.
4. "COPAXONE®" in *Physician's Desk Reference*, Thompson Reuters—Physician's Desk Reference Inc., Montvale, N.J., 2008, 3110-3113.
5. Yong (2002) "Differential mechanisms of action of interferon-β and glatiramer acetate in MS" *Neurology*, 59:1-7.

What is claimed is:

1. A method of injecting a dosage of a medicament formulation from a syringe loaded within an injector device, the syringe having a needle, the injector device including a first half assembly and a second half assembly, the second half assembly including a rear outer cover, a plunger ram disposed within the rear outer cover, a firing button carried by the rear outer cover, and an inner body disposed within the rear outer cover and fully disposed within the injector device, the inner body being movable within the rear outer cover, the method comprising:
   inserting a front end of the first half assembly into a front end of the second half assembly to push the plunger ram to a cocked position;
   inserting a prefilled syringe at the first half assembly;
   assembling the injector device by rotatably coupling a rear of the first half assembly to the front end of the second half assembly;
   moving the inner body relative to the firing button by pressing an abutment end of the injector device against an injection site; and
   actuating the firing button to release a plunger ram biased towards the syringe and thereby inject the dosage at the injection site.

2. The method of claim 1, wherein actuating the firing button includes depressing the firing button.

3. The method of claim 2, wherein moving the inner body relative to the firing button includes moving the inner body against the bias of a return spring disposed in the rear outer cover.

4. The method of claim 1, wherein the rear outer cover and inner body are disposed in the second half assembly of the injector device.

5. The method of claim 4, wherein a forwardly extending arm of the inner body is in contact with the first half assembly during injection.

6. The method of claim 1, wherein actuating the firing button includes moving the firing button from an undepressed position to a depressed position relative to the rear cover and relative to the inner body; and wherein the firing button is biased to the undepressed position.

7. The method of claim 1, further comprising adjusting an amount the needle of the syringe extends beyond the injector device during injection.

8. The method of claim 1, wherein assembling the injector device comprises aligning a first alignment indicator of the first half assembly with a second alignment indicator of the second half assembly.

9. The method of claim 1, wherein moving the inner body relative to the firing button comprises moving the inner body closer to the firing button.

10. The method of claim 1, wherein the injector device has a longitudinal axis extending from the abutment end to an opposite end, wherein depressing the firing button includes moving the firing button along the longitudinal axis.

11. The method of claim 1, wherein the firing button is disposed at the rear housing.

12. The method of claim 11, wherein the firing button is disposed at the opposite end of the injector device from the abutment end.

13. The method of claim 11, wherein the firing button is directly coupled to the rear outer cover.

14. The method of claim 1, wherein the first half assembly and the second half assembly have unequal lengths.

15. The method of claim 14, wherein the first half assembly and the second half assembly have substantially different lengths.

16. The method of claim 14, wherein the second half assembly is longer than the first half assembly.

17. The method of claim 1, wherein moving the inner body relative to the firing button enables movement of the plunger ram relative to the inner body.

18. The method of claim 17, further comprising releasing the plunger ram for movement in response to moving the inner body relative to the firing button by pressing the abutment end of the injector device against the injection site.

19. The method of claim 17, further comprising moving the plunger ram along a path of travel in response to releasing the plunger ram for movement.

20. The method of claim 19, wherein the inner body moves parallel to the path of travel when the inner body is moved relative to the firing button.

21. The method of claim 17, further comprising actuating the firing button after moving the inner body relative to the firing button by pressing an abutment end of the injector device against an injection site.

22. The method of claim 1, further comprising damping the prefilled syringe against shock, wherein the syringe has a barrel and a flange, and the act of damping the prefilled syringe comprises cushioning the flange.

23. The method of claim 22, wherein the syringe is operably connected to a carrier, the carrier is movable within the first half assembly, and a damper is positioned between at least a part of the syringe and at least a part of the carrier, the method further comprising cushioning movement between the syringe and the carrier.

24. The method of claim 1, wherein the injector device has a proximal end and a distal end, the abutment end being located at the distal end, the syringe has a barrel and a plunger, and the first half assembly includes a carrier movable within the first half assembly and a carrier spring biasing the carrier toward the proximal end of the injector device, the method further comprising:
upon actuating the firing button, urging the plunger ram against the plunger;
at least partially compressing the carrier spring by moving the barrel and plunger together as a unit relative to the distal end of the injector device without moving the plunger relative to the barrel; and then
moving the plunger relative to the barrel.

25. The method of claim 1, wherein a sheath remover is operably coupled to the front end of the first half assembly; and wherein inserting a front end of the first half assembly into a front end of the second half assembly to push the plunger ram to a cocked position comprises:
positioning the first half assembly so that the front end of the first half assembly faces the second half assembly; and
inserting the sheath remover into the second half assembly;
sliding the sheath remover within the inner body, and
pressing the sheath remover against the plunger ram to move the plunger ram against a bias of a main spring from a deployed position to a cocked position.

26. The method of claim 1 further comprising injecting a dose of the medicament formulation, the dose of medicament formulation including a Glatiramer acetate.

27. A method of injecting a dosage of a medicament formulation including Glatiramer acetate from a syringe loaded within an injector device, the syringe having a needle, the injector device including a first half assembly and a second half assembly, the second half assembly including a rear outer cover, a plunger ram disposed within the rear outer cover, a firing button carried by the rear outer cover, and an inner body disposed within the rear outer cover and fully disposed within the injector device, the inner body being movable within the rear outer cover, the method comprising:
inserting a front end of the first half assembly into a front end of the second half assembly to push the plunger ram along a path of travel to a cocked position; retaining the plunger ram at the cocked position against a bias of a main spring;
inserting a prefilled syringe at the first half assembly;
assembling the injector device, the assembling including rotatably coupling a rear end of the first half assembly to the front end of the second half assembly;
pressing an abutment end of the injector device against an injection site;
moving the inner body relative to the firing button and parallel to the path of travel;
enabling release of the plunger ram from the cocked position in response to moving the inner body relative to the firing button;
moving the firing button relative to the rear outer cover; and
moving the plunger ram along the path of travel under the bias of the main spring in response to moving the firing button relative to the rear outer cover, the main spring moving the plunger ram along the path of travel towards the syringe.

* * * * *